(12) United States Patent
Aoki et al.

(10) Patent No.: US 8,052,977 B2
(45) Date of Patent: Nov. 8, 2011

(54) DNA VACCINE FOR KOI HERPES VIRUS (KHV) DISEASE

(75) Inventors: Takashi Aoki, Tokyo (JP); Ikuo Hirono, Tokyo (JP)

(73) Assignee: National University Corporation Tokyo University of Marine Science and Technology (JP)

( * ) Notice: Subject to any disclaimer, the term of this patent is extended or adjusted under 35 U.S.C. 154(b) by 73 days.

(21) Appl. No.: 12/296,459

(22) PCT Filed: Jan. 30, 2007

(86) PCT No.: PCT/JP2007/051498
§ 371 (c)(1),
(2), (4) Date: Nov. 12, 2008

(87) PCT Pub. No.: WO2007/119279
PCT Pub. Date: Oct. 25, 2007

(65) Prior Publication Data
US 2009/0060951 A1 Mar. 5, 2009

(30) Foreign Application Priority Data
Apr. 13, 2006 (JP) ................................ 2006-111414

(51) Int. Cl.
*A61K 39/12* (2006.01)
(52) U.S. Cl. ......................................... 424/199.1; 435/5
(58) Field of Classification Search ............... 424/199.1; 435/5
See application file for complete search history.

(56) References Cited

U.S. PATENT DOCUMENTS
7,351,527 B2 * 4/2008 Kotler et al. ................. 435/5
2006/0013828 A1 * 1/2006 Kotler et al. ............... 424/199.1

FOREIGN PATENT DOCUMENTS
JP 2003-155254 5/2003
JP 2005-112726 4/2005

OTHER PUBLICATIONS

Gray et al, Journal of Fish Diseases, 2002, vol. 25, pp. 171-178.*
Boudinot P. et al., "Combined DNA immunization with the glycoprotein gene of viral hemorrhagic septicemia Virus and infectious hematopoietic necrosis Virus induces double-specific protective immunity and nonspecific response in rainbow trout," Virology, 1998, vol. 249, p. 297-306.
Database DDBJ/EMBL/GenBank online, Accession No. Q75N32, <<http://www.ncbi.nlm.nih.gov/entrez/viewer.fcgi?75553604:CAGE__DDBJ:1316278>> Jul. 5, 2004 uploaded, Kurita J. et al., Definition: Hypothetical protein.
Database DDBJ/EMBL/GenBank online, Accession No. Q75N31, <<http://www.ncbi.nlm.nih.gov/entrez/viewer.fcgi?75553603:CAGE__DDBJ:1316277>> Jul. 5, 2004 uploaded, Kurita J. et al., Definition: Membrane protein.
Database DDBJ/EMBL/GenBank online, Accession No. Q75N28, <<http://www.ncbi.nlm.nih.gov/entrez/viewerfcgi?75553600:CAGE__DDBJ:1316 274>> Feb. 1, 2005 uploaded, Kurita J. et al., Definition: Hypothetical protein.
Database DDBJ/EMBL/GenBank online, Accession No. Q75N51, <<http://www.ncbi.nlm.nih.gov/entrez/viewerfcgi?75553606:CAGE__DDBJ:1316 280>> Jul. 5, 2004 uploaded, Kurita J. et al., Definition: Membrane protein.
Waltzek et al., "Koi herpesvirus represents a third cyprinid herpesvirus (Cy1-1V-3) in the family *Herpesviridae*," Journal of General Virology, 86, pp. 1659-1667, 2005.
Ronen et al., "Efficient vaccine against the virus causing a lethal disease in cultured *Cyprinus Carpio*," Vaccine 21, pp. 4677-4684, 2003.
Kurita et al., "Cyprinid herpesvirus 3 ORF1, ORF2, ORF3, ORF4, ORF5 genes for hypothetical protein, membrane protein, membrane protein, major envelope protein, hypothetical protein, complete cds, strain: KHVO301," database EMBL (Online), XP002602385 Database accession No.EM__VI:AB178537, May 10, 2004.
Kurita et al., "Cyprinid herpesvirus 3 genes for membrane protein, major envelope protein, hypothetical protein, complete cds," database EMBL (Online), XP002602386 Database accession No. EM__VI:AB178324, May 1, 2004.
European Search Report issued in European Application No. 07707716.2, dated Oct. 15, 2010.

* cited by examiner

*Primary Examiner* — Ali R. Salimi
(74) *Attorney, Agent, or Firm* — Kenneth H. Sonnenfeld; Margaret B. Brivanlou; King & Spalding LLP

(57) ABSTRACT

The present invention provides a DNA vaccine for carps for inducing protective immunity against Koi herpesvirus (KHV). The DNA vaccine comprises a DNA comprising a nucleotide sequence encoding an immunogenic polypeptide against Koi herpesvirus (KHV) of carps, or an expression vector comprising the DNA as an active ingredient.

2 Claims, 2 Drawing Sheets

(A)

(B)

DNA VACCINE FOR KOI HERPES VIRUS (KHV) DISEASE

TECHNICAL FIELD

The present invention relates to a DNA vaccine for inducing protective immunity against infection of Koi herpesvirus (KHV) to fishes.

BACKGROUND ART

Koi herpesvirus disease is a disease that develops in black carps (Magoi) or colored carps (Nishikigoi) by being infected with Koi herpesvirus (KHV). When the disease is developed, the fishes' motion becomes slower or their appetite decreases. There is no remarkable visible symptom, but color degradation or erosion (sore) of brachia is observed. It is a disease developed from immature fishes to mature fishes, with high mortality rate.

The Koi herpesvirus disease was reported for the first time in May 1998, in Israel. Later, also in Israel, the disease has been reported twice, in autumn of the same year and in the next spring, and about 600 tons of carps, including those for exportation, died. The total damage exceeded 4 million U.S. dollars. After that, many onsets have been reported successively in many countries around the world including Israel, Great Britain, Germany, Netherlands, Belgium, United States, Indonesia, and Taiwan.

In November 2003, the Ministry of Agriculture, Forestry and Fisheries of Japan announced that carps suspected of being infected by Koi herpesvirus disease have been observed in Kasumigaura, Ibaraki prefecture. After which, onsets of Koi herpesvirus have been reported in various regions of the country, including Aomori, Yamanashi, Mie, Okayama and Miyazaki. The Ministry of Agriculture, Forestry and Fisheries is currently making efforts to determine the infection pathway of the disease as well as to prevent dispersion of this disease.

Though some vaccines for fish and shellfish have been developed for bacterial infection, there are almost none for viral or parasitic diseases other than the vaccine against iridovirus in some salmonids and Perciformes (for example, see patent document 1).

Generally, vaccines are used to prevent or treat viral infections. Vaccines include inactivated vaccines (Japanese encephalitis, Weil's disease, etc.), toxoids (tetanus, diphtheria, etc.), attenuated vaccines (BCG, polio, etc.), recombinant vaccines (hepatitis B, etc.). Inactivated vaccines and toxoids, which have detoxified exotoxins, are relatively safe vaccines that induce antibody production. Recombinant vaccines on the other hand do not contain impurities compared to inactivated vaccines, and are believed to be safer vaccines. The only vaccines for fisheries currently authorized in Japan are inactivated vaccines against *Vibrio* disease, alpha-hemolytic *Streptococcus* disease, iridovirus and beta-hemolytic *Streptococcus*.

Although these vaccines can induce antibody production, cellular immunity is hardly induced, which is a deficit. Moreover, it is commercially necessary to obtain large amount of virus to be the antigens for inactivated vaccines and attenuated vaccines, and it is essential to secure appropriate viral particles. Moreover, in many cases, immune effect obtained with attenuated vaccines is maintained for a long period of time, and so are the side-effects or risks. As for inactivated and recombinant vaccines, the maintenance of antigens is thought to be short in hosts, and adjuvants or the like are therefore needed. All these conventional types of vaccines need refrigeration from manufacture until inoculation to a subject. As such, problems of cost increase and decrease in effect are encountered.

Recently, research and development of vaccines are proceeding creating new types of vaccines. DNA vaccine is a leading new generation vaccine done by administering a plasmid DNA encoding an immunogenic protein to the host. With DNA vaccine, disadvantages of conventional vaccines, as described in the following, have been addressed. These DNA vaccines can induce strongly not only humoral immune response but also cellular immune responses; can endow protective ability against infections; can be purified in large amounts; and because it is stable at room temperature or under high temperature, it does not require refrigeration and have a longer shelf-life. Furthermore, construction or change of DNA vaccines can be readily made by genetic engineering, hence the time necessary to develop it is shortened.

As examples, there have been reports on intramuscular injection of a gene encoding glycoprotein, a constituent protein of Rhabdovirus, stimulating immune response of *Oncorhynchus mykiss* (for example, see non-patent document 1), and of DNA vaccines (for example, see non-patent document 2); of DNA vaccines against viral hemorrhagic septicemia of *Paralichthys olivaceus* (for example, see patent document 2); or of DNA vaccines against virus encoding apoptosis-inducing protein of infectious hemapatopoietic necrosis (IHN) virus (for example, see patent document 3); or of DNA vaccines for cultured types using genetic expression system that can induce expression of an immunogenic polypeptide (for example, see patent document 4). However, DNA vaccines for stimulating protective immunity against Koi herpes virus of carps have not yet been reported.

[Patent document 1] Japanese Laid-Open Patent Application No. 9-176043
[Patent document 2] Japanese Laid-Open Patent Application No. 2005-112726
[Patent document 3] Japanese Laid-Open Patent Application No. 2002-125674
[Patent document 4] Japanese Laid-Open Patent Application No. 9-285291
[Non-Patent document 1] P. Boudinot et. al, Virology, (USA), 1998, Vol. 249, p. 297-306
[Non-Patent document 2] McLauchlan et. al, Fish and Shellfish Immunology, England, 2003, Vol. 15, p. 39-50

DISCLOSURE OF THE INVENTION

Object to be Solved by the Invention

The object of the present invention is to provide a DNA vaccine for carps for inducing protective immunity against Koi herpesvirus (KHV).

Means to Solve the Object

The present inventors made a keen study to develop an effective vaccine against Koi herpesvirus (KHV). They determined all of the nucleotide sequences of each Koi herpesvirus (KHV) gene DNA sampled from Japan, United States, Israel and Indonesia. Among the approximately 180 genes, they selected 5 types of genes encoding glycoprotein of Koi herpesvirus (KHV) and 5 types of genes encoding membrane proteins, and inoculated (intramuscular injection) the plasmid DNA carrying these genes to carps, and found out that these genes had protected carps against Koi herpesvirus (KHV). Thus, the present invention has been completed.

The present invention relates to (1) a DNA encoding (a) a glycoprotein of Koi herpesvirus (KHV) consisting of the amino acid sequence as shown by SEQ ID NO: 2, 4, 6, 8 or 10; (b) a protein consisting of an amino acid sequence wherein one or a few amino acids are deleted, substituted, or added in the amino acid sequence as shown by SEQ ID No: 2, 4, 6, 8 or 10, and having immunogenicity to Koi herpesvirus (KHV); or (c) a protein consisting of an amino acid sequence being 80% homologous or more with the amino acid sequence as shown by SEQ ID NO: 2, 4, 6, 8 or 10, and having immunogenicity to Koi herpesvirus (KHV); (2) a DNA consisting of the nucleotide sequence as shown by SEQ ID NO: 1, 3, 5, 7 or 9, or its complementary sequence; (3) a DNA consisting of the nucleotide sequence wherein one or a few nucleotides are deleted, substituted, or added in the nucleotide sequence as shown by SEQ ID NO: 1, 3, 5, 7 or 9, and encoding a protein having immunogenicity to Koi herpesvirus (KHV); (4) a DNA hybridizing, under stringent conditions, with a DNA consisting of a sequence complementary to the nucleotide sequence as shown by SEQ ID NO: 1, 3, 5, 7 or 9, and encoding a protein having immunogenicity to Koi herpesvirus (KHV); (5) a DNA encoding (d) a membrane protein of Koi herpesvirus (KHV) consisting of the amino acid sequence as shown by SEQ ID NO: 12, 14, 16, 18 or 20; (e) a protein consisting of an amino acid sequence wherein one or a few amino acids are deleted, substituted, or added in the amino acid sequence as shown by SEQ ID NO: 12, 14, 16, 18 or 20, and having immunogenicity to Koi herpesvirus (KHV); or (f) a protein consisting of an amino acid sequence being 80% homologous or more with the amino acid sequence as shown by SEQ ID NO: 12, 14, 16, 18 or 20, and having immunogenicity to Koi herpesvirus (KHV).

Moreover, the present invention relates to (6) a DNA consisting of the nucleotide sequence as shown by SEQ ID NO: 11, 13, 15, 17 or 19, or its complementary sequence; (7) a DNA consisting of a nucleotide sequence wherein one or a few nucleotides are deleted, substituted or added in the nucleotide sequence as shown by SEQ ID NO: 11, 13, 15, 17 or 19, and encoding a protein having immunogenicity to Koi herpesvirus (KHV); (8) a DNA hybridizing, under stringent conditions, with a DNA consisting of a sequence complementary to the nucleotide sequence as shown by SEQ ID NO: 11, 13, 15, 17 or 19, and encoding a protein having immunogenicity to Koi herpesvirus (KHV); (9) a glycoprotein of Koi herpesvirus (KHV) consisting of the amino acid sequence as shown by SEQ ID NO: 2, 4, 6, 8, or 10; (10) a protein consisting of an amino acid sequence wherein one or a few amino acids are deleted, substituted, or added in the amino acid sequence as shown by SEQ ID NO: 2, 4, 6, 8, or 10, and having immunogenicity to Koi herpesvirus (KHV); (11) a membrane protein of Koi herpesvirus (KHV) consisting of the amino acid sequence as shown by SEQ ID NO: 12, 14, 16, 18, or 20; (12) a protein consisting of an amino acid sequence wherein one or a few amino acids are deleted, substituted or added in the amino acid sequence as shown by SEQ ID NO: 12, 14, 16, 18 or 20, and having immunogenicity to Koi herpesvirus (KHV).

Furthermore, the present invention relates to (13) a recombinant vector comprising 1 or more DNAs selected from the DNA according to any one of (1) to (8); (14) a DNA vaccine for carps comprising 1 or more DNAs selected from the DNA according to any one of (1) to (8); (15) the DNA vaccine for carps comprising the recombinant vector according to (13); (16) a method for preventing or treating Koi herpesvirus (KHV), wherein the DNA vaccine for carps according to (14) or (15) is administered to a carp; (17) a method for using the DNA vaccine for carps according to (14) or (15), to induce immune response of carps to Koi herpesvirus (KHV); (18) an antibody recognizing specifically the protein according to any one of (9) to (12); (19) a transgenic carp having resistance to Koi herpesvirus (KHV), obtained by introducing a gene expression vector for expressing the protein according to any one of (9) to (12).

Figure 1:
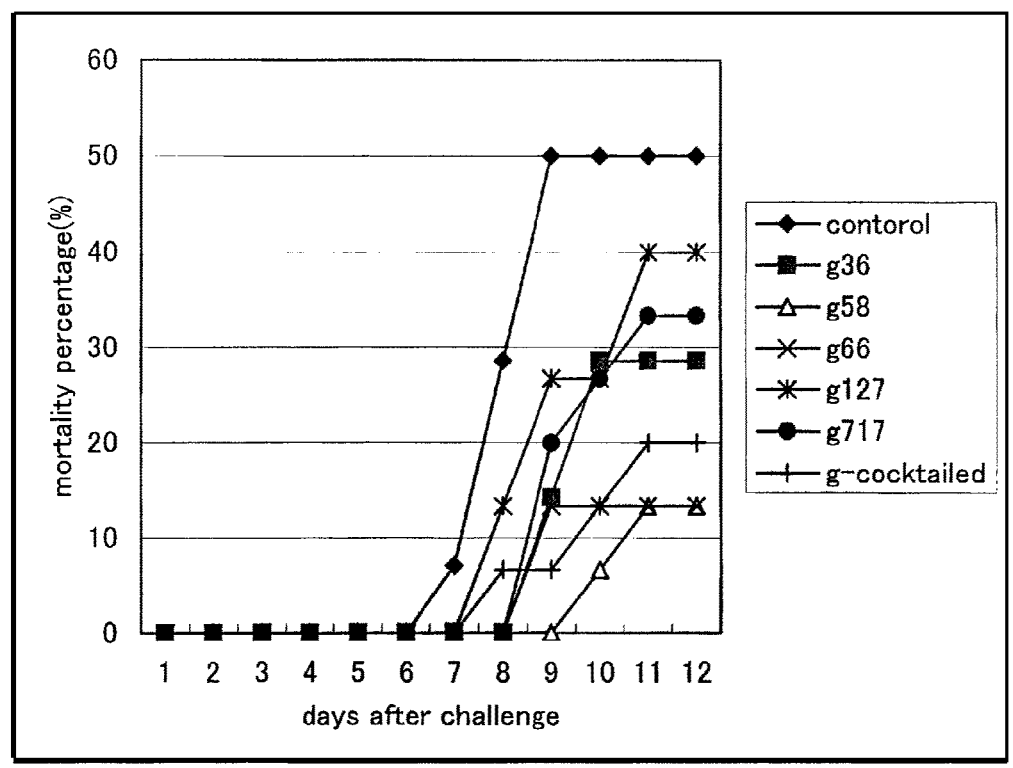
FIG. 1 Figure showing the DNA vaccine test results against KHV infections.
Figure 1:
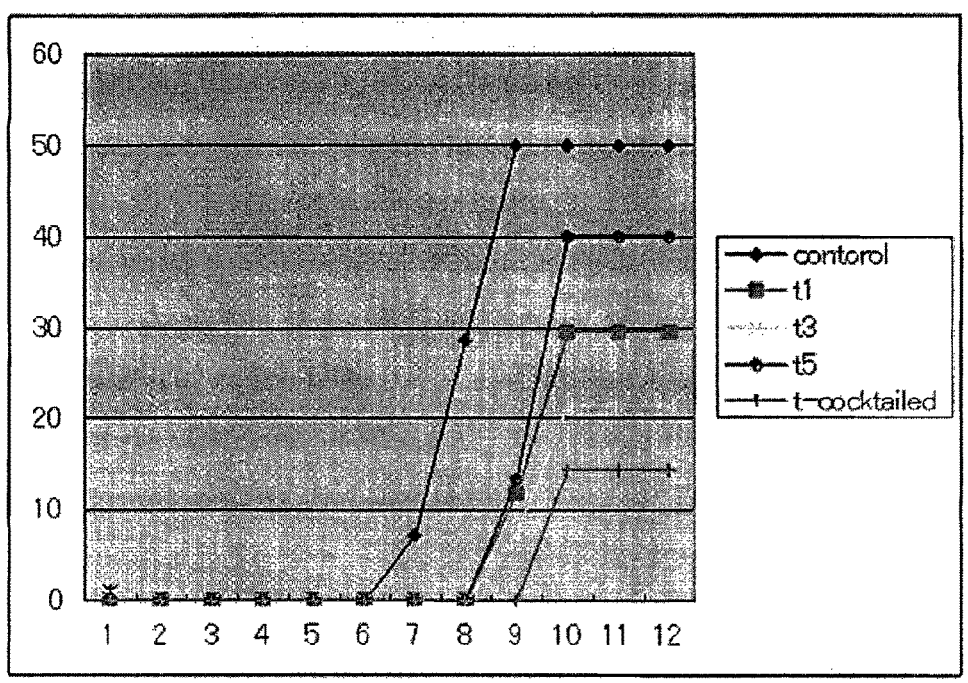
Figure 2:
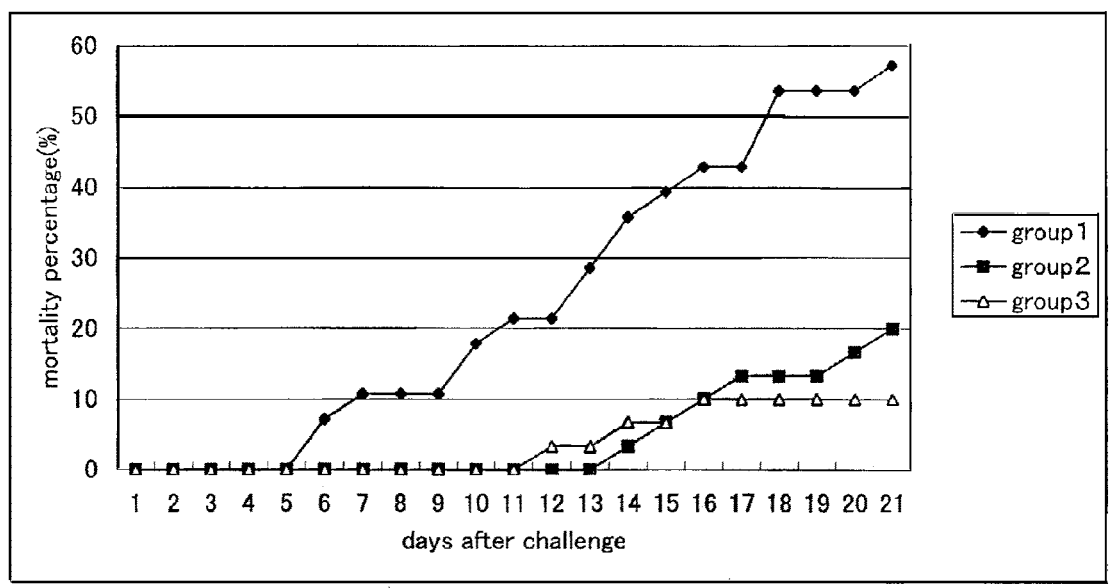

(A) test results when 5 types of glycoprotein genes were administered, respectively (B) test results when 3 types of membrane protein genes were administered, respectively FIG. 2 Figure showing the test result using DNA mixed vaccine against KHV infection. The vertical axis shows the accumulated mortality rate, and the horizontal axis show the number of days after KHV infection. Group 1 is the negative control test area, Group 2 is the membrane protein test area, and Group 3 is glycoprotein test area.

BEST MODE FOR CARRYING OUT THE INVENTION

Best Mode of Practicing the Present Invention

For the DNA of the present invention, there is no specific limitation as long as it is: (a) a DNA encoding glycoprotein of Koi herpesvirus (KHV) consisting of the amino acid sequence as shown by SEQ ID NO: 2, 4, 6, 8 or 10; (b) a DNA consisting of an amino acid sequence wherein one or a few amino acids are deleted, substituted or added in the amino acid sequence as shown by SEQ ID NO: 2, 4, 6, 8 or 10, and encoding a protein having immunogenicity to Koi herpesvirus (KHV); (c) a DNA consisting of an amino acid sequence being 80% homologous or more with the amino acid sequence as shown by SEQ ID NO: 2, 4, 6, 8, or 10, and encoding a protein having immunogenicity to Koi herpesvirus (KHV); a DNA consisting of the nucleotide sequence (base sequence) as shown by SEQ ID No: 1, 3, 5, 7 or 9, or its complementary sequence; a DNA consisting of a nucleotide sequence wherein one or a few nucleotides (bases) are deleted, substituted or added in the nucleotide sequence as shown by SEQ ID NO: 1, 3, 5, 7 or 9, and encoding a protein having immunogenicity to Koi herpesvirus (KHV); a DNA hybridizing under stringent conditions with a DNA consisting of a sequence complementary to the nucleotide sequence as shown by SEQ ID No: 1, 3, 5, 7 or 9, and encoding a protein having immunogenicity to Koi herpesvirus (KHV); (d) a DNA encoding a membrane protein of Koi herpesvirus (KHV) consisting of the amino acid sequence as shown by SEQ ID NO: 12, 14, 16, 18 or 20; (e) a DNA consisting of an amino acid sequence wherein one or a few amino acids are deleted, substituted or added in the amino acid sequence as shown by SEQ ID NO: 12, 14, 16, 18 or 20, and encoding a protein having immunogenicity to Koi herpesvirus (KHV); (f) a DNA consisting of an amino acid sequence being 80% homologous or more with the amino acid sequence as shown by SEQ ID NO: 12, 14, 16, 18 or 20 and encoding a protein having immunogenicity to Koi herpesvirus (KHV); a DNA consisting of the nucleotide sequence as shown by SEQ ID NO: 11, 13, 15, 17 or 19, or its complementary sequence; a DNA consisting of a nucleotide sequence wherein one or a few nucleotides are deleted, substituted or added in the nucleotide sequence as shown by SEQ ID No: 11, 13, 15, 17 or 19, and encoding a protein having immunogenicity to Koi herpesvirus (KHV); or a DNA hybridizing under stringent conditions with a DNA consisting of a sequence complementary to the nucleotide sequence as shown by SEQ ID NO: 11, 13, 15, 17 or 19, and encoding a protein having immunogenicity to Koi herpesvirus (KHV).

Further, for the protein of the present invention, there is no specific limitation as long as it is a glycoprotein of Koi herpesvirus (KHV) consisting of the amino acid sequence as shown by SEQ ID NO: 2, 4, 6, 8 or 10; a protein consisting of an amino acid sequence wherein one or a few amino acids are deleted, substituted, or added in the amino acid sequence as shown by SEQ ID NO: 2, 4, 6, 8 or 10, and having immunogenicity to Koi herpesvirus (KHV); a membrane protein of Koi herpesvirus (KHV) consisting of the amino acid sequence as shown by SEQ ID NO: 12, 14, 16, 18 or 20; or a protein consisting of an amino acid sequence wherein one or a few amino acids are deleted, substituted or added in the amino acid sequence as shown by SEQ ID NO: 12, 14, 16, 18, or 20, and having immunogenicity to Koi herpesvirus (KHV). A protein having immunogenicity to Koi herpesvirus in the present invention, relates to a protein that can stimulate/induce immunity (including humoral immunity and cellular immunity) against Koi herpesvirus (KHV) in vivo, when introduced into the body of a carp.

The phrase "amino acid sequence wherein one or a few amino acids are deleted, substituted or added" mentioned above relates to an amino acid sequence wherein, any numbers of amino acids, for example, 1 to 20 (preferably 1 to 15; more preferably 1 to 10; most preferably 1 to 5) amino acids are deleted, substituted or added. Moreover, the phrase "nucleotide sequence wherein one or a few nucleotides are deleted, substituted or added" mentioned above relates to a nucleotide sequence wherein, any numbers of nucleotides, for example, 1 to 20 (preferably 1 to 15; more preferably 1 to 10; most preferably 1 to 5) nucleotides are deleted, substituted or added.

For example, a DNA consisting of a nucleotide sequence wherein one or a few nucleotides are deleted, substituted or added (mutated DNA) can be prepared by any method known to a person skilled in the technique, including chemical synthesis, genetic engineering method and mutagenesis. Specifically, mutated DNA can be obtained by ultraviolet ray irradiation, or genetic engineering method, or the like. These methods introduce mutation to DNAs, including a DNA consisting of the nucleotide sequence as shown by SEQ ID NO: 1, 3, 5, 7 or 9; or a DNA comprising the nucleotide sequence as shown by SEQ ID NO: 11, 13, 15, 17 or 19. The method for inducing site-specific mutation, which is one of genetic engineering methods, is useful in introducing a particular mutation to a particular site. The method can be performed according to the methods described in Molecular Cloning: A Laboratory Manual, 3rd Ed., Cold Spring Harbor Laboratory, Cold Spring Harbor, N.Y., 2001 (hereinafter referred to as "Molecular cloning, 3rd Ed."), Current Protocols in Molecular Biology, Supplement 1-38, John Wiley & Sons (1987-1997), etc. By expressing the mutated DNA using an appropriate protein expression system, a protein consisting of an amino acid sequence, wherein one or a few amino acids are deleted, substituted or added can be obtained.

The phrase "nucleotide sequence hybridizing under stringent conditions" mentioned above, relates to a nucleotide sequence that can be obtained by using nucleic acids such as DNA or RNA as a probe, by colony hybridization, plaque hybridization, or Southern blot hybridization methods. Specifically, a DNA can be identified by hybridizing the probe with DNA derived from a colony or plaque, or a fragment of the DNA fixed in a filter, in the presence of 0.7 to 1.0 M of NaCl, at 65° C., and then by washing the filter with SSC solution in an amount of about 0.1 to 2 fold (composition of 1-fold concentration of SSC solution: 150 mM sodium chloride, 15 mM sodium citrate), at 65° C. Hybridization can be performed according to the method described in Molecular Cloning, 3rd Ed., etc.

In other words, the phrase "under stringent conditions" relates to a condition in which a so-called specific hybrid is formed, and that a non-specific hybrid is not formed, and specifically, a condition in which DNAs being mutually 50 to 70% homologous or more hybridize, while DNAs being less homologous do not hybridize, or a hybridization condition that are washing conditions for common Southern hybridization, that is at 65° C., with a salt concentration equivalent to 1×SCC, 0.1% SDS, or 0.1×SSC, 0.1% SDS, can be exemplified. For example, DNA hybridizing under stringent conditions, a DNA being homologous at a certain level or more with the nucleotide sequence of a DNA used as a probe, for example, a DNA being 60% homologous or more, preferably 70% or more, more preferably 80% or more, further preferably 90% or more, particularly preferably 95% or more, and most preferably 98% homologous or more, can be preferably exemplified.

The method for obtaining or preparing a DNA of the present invention is not particularly limited, and it can be prepared according to common methods by chemical synthesis, by preparing appropriate probes or primers according to the nucleotide sequence information as shown by SEQ ID NO: 1, 3, 5, 7 or 9; or SEQ ID NO: 11, 13, 15, 17 or 19, or to the amino acid sequence information as shown by the amino acid sequence as shown by SEQ ID NO: 2, 4, 6, 8 or 10; or SEQ ID NO: 12, 14, 16, 18 or 20, disclosed in the present specification, and by screening DNA library of Koi herpesvirus (KHV).

The method for obtaining or preparing a protein of the present invention is not particularly limited, and it can be any one of naturally-occurring proteins, chemically synthesized proteins, or recombinant proteins prepared by genetic engineering method. When obtaining a naturally-occurring protein, a protein of the present invention can be obtained from cells or tissues expressing the protein by combining appropriate methods for separating/purifying a protein. When preparing proteins by chemical synthesis, a protein of the present invention can be synthesized according to chemical synthesis method such as Fmoc method (fluorenylmethyloxycarbonyl method) and tBoc method (t-Butyloxycarbonyl method), or it can be synthesized by using various peptide synthesizers, available commercially. When preparing a protein by genetic engineering technology, a protein of the present invention can be prepared by introducing a DNA consisting of the nucleotide sequence encoding the protein to the appropriate expression system. Among these, preparation by genetic engineering technology where it is possible to prepare a large amount with a relatively easy process, is preferred.

For example, when preparing a protein of the present invention by genetic engineering technology, known methods including ammonium sulfate or ethanol precipitation, acid extraction, anion or cation exchange chromatography, phosphocellulose chromatography, hydrophobic interactive chromatography, affinity chromatography, hydroxyapatite chromatography and lectin chromatography (preferably high performance liquid chromatography) is used. For a column to be used in affinity chromatography, for example, using a column to which antibodies such as monoclonal antibodies to a protein of the present invention, or, a column to which a substance having affinity to the peptide tag, when a normal peptide tag is added to a protein of the present invention, purified substances of these proteins can be obtained. Further, when a protein of the present invention is expressed on the cell membrane, the purified samples can be obtained by performing the above mentioned purifying treatment, after allowing cell membrane degrading enzyme to react.

Further, as for a protein consisting of an amino acid sequence wherein one or a few amino acids are deleted, substituted, or added in the amino acid sequence as shown by SEQ ID NO: 2, 4, 6, 8 or 10, or SEQ ID NO: 12, 14, 16, 18 or 20, or a protein consisting of an amino acid sequence being 80% homologous or more with the amino acid sequence as shown by SEQ ID NO: 2, a person skilled in the technique could prepare or obtain it appropriately according to the nucleotide sequence information as shown by SEQ ID NO: 1, 3, 5, 7 or 9, or SEQ ID NO: 11, 13, 15, 17 or 19, showing one example of the nucleotide sequence encoding the amino acid sequence as shown by SEQ ID No: 2, 4, 6, 8 or 10, or SEQ ID NO: 12, 14, 16, 18 or 20, respectively.

For the recombinant vector of the present invention, there is no specific limitation as long as it is a recombinant vector comprising the above-mentioned gene DNA of the present invention, that can express a protein having immunogenicity to Koi herpesvirus (KHV) in the body of a carp. A recombinant vector of the present invention can be constructed by integrating appropriately the gene DNA of the present invention into an expression vector. As for expression vectors, those being able to self replicate in host cells, or those integratable to chromosomes of host cells are preferred, and those comprising regulatory sequence such as promoter, enhancer, terminator, etc. at a position where the gene of the present invention can be expressed, can be used preferably. As for expression vectors, expression vectors for animal cells, particularly recombinant vectors using expression vector for fish cells are preferred. As for the procedures and methods for constructing expression vectors that can be used in the present invention, those commonly used in the field of genetic engineering can be used.

For regulatory sequences that can be used in the present invention, constitutive promoter, inductive or adjustable promoter, tissue-specific promoter, or promoter derived from genes of the expressed antigen can be used. However, it is not limited to these as long as the regulatory sequence can be expressed in fish cells. As for constitutive promoter, promoter sequence derived from cytomegarovirus (CMV), or strong promoters such as Rous sarcoma virus (RSV), simian virus-40 (SV-40), muscular β-actin promoter, or simplex herpes virus (HSV) can be used. As for tissue-specific promoters, thimidine kinase promoter can be exemplified. As for inductive or adjustable promoters, growth-hormone adjustable promoter, promoter being under control of the 1ac operon sequence, or zinc-inducible metallothionein promoter can be used. The transcriptional regulatory sequence can be bound to a nucleotide sequence encoding immunogenic polypeptide, operably (i.e., so that it can control the nucleotide sequence expression).

The regulatory sequence can comprise an expression regulating sequence including DNA sequence of a promoter (for example, the above mentioned inducible or constructive promoter), and can further include one or more copies of enhancer element, intron sequence for splicing transcription or polyadenylated signal [for example, derived from simian virus-40 (SV-40) or from bovine growth hormone), or immunostimulatory DNA sequence known as CpG motif, according to need.

Further, according to need, an expression vector can comprise for example, a bacterial replication origin sequence, or selective markers such as antibiotic resistant (e.g. kanamycin, etc.) gene or antibiotic non-resistant gene (e.g. β-galactosidase gene).

For the DNA vaccine for carps of the present invention, there is no specific limitation as long as it is a composition comprising one or more DNA selected from the DNAs of the present invention, or a composition comprising the recombinant vector of the present invention. However, 5 types of DNA cocktails consisting of the nucleotide sequence as shown by SEQ ID NOs: 1, 3, 5, 7 and 9, 5 types of DNA cocktails consisting of the nucleotide sequences as shown by SEQ ID NOs: 11, 13, 15, 17 and 19, these 10 types of DNA cocktails, or recombinant vectors that can express these DNA cocktails are preferred. Furthermore, adjuvants can be added/combined to the DNA vaccine for carps of the present invention. Adjuvants enhance immune response against antigens by stimulating the immune system, and are mainly added to vaccines, as an auxiliary substance. Typical adjuvants include aluminium compounds, polynucleotides, or bacterial cell components of bacteria. Koi IL-1β or zebra IFN-α can be preferably used. These can be inoculated to fishes with the vaccine of the present invention by preparing plasmids in which IL-1β gene or IFN-α gene is introduced so that it can be expressed in the body of a carp.

By administering a DNA vaccine for carps of the present invention, an immune response against Koi herpesvirus (KHV) disease of a carp can be induced, and Koi herpesvirus (KHV) disease can be prevented or treated. As for fishes to which the DNA vaccine for carps of the present invention can be applied, there is no specific limitation as long it is a fish that can be infected by Koi herpesvirus (KHV), and black carps and colored carps can be specifically used.

As for antibodies binding specifically to a protein of the present invention, immune-specific antibodies including monoclonal antibodies, polyclonal antibodies, chimeric antibodies, single stranded antibodies, humanized antibodies can be specifically used, and these can be prepared according to common methods by using the above-mentioned glycoprotein or membrane protein as an antigen. However, among these, monoclonal antibodies are preferred from the point of its specificity. Antibodies binding specifically to a protein of the present invention such as the monoclonal antibodies are, for example, useful to separate/quantify a protein of the present invention, or to clarify the molecular mechanism of a protein of the present invention.

Antibodies against a protein of the present invention are produced by administering a protein or fragments comprising epitope, or cells wherein the protein is expressed on the cell membrane, to animals (preferably other than human) by using commonly used protocol. As for preparation of monoclonal antibodies, hybridoma method (Nature 256, 495-497, 1975), trioma method, human B cells hybridoma method (Immunology Today 4, 72, 1983) and EBV-hybridoma method (Monoclonal Antibodies and Cancer Therapy, pp. 77-96, Alan R. Liss, Inc., 1985) that can yield antibodies generated by cultures of continuous cell lines, can be used.

Further, the function of the above-mentioned protein can be analyzed by using fluorescent substances such as FITC (Fluoresceinisothiocyanate) or tetramethylrhodamineisocyanate, radioisotopes such as $^{125}$I, $^{32}$P, $^{14}$C, $^{35}$S or $^{3}$H, those labeled with enzymes such as alkaliphosphatase, peroxidase, β-galactosidase, phycoerythrin, or fused proteins fused with fluorescent proteins such as green fluorescent protein (GFP), to the antibodies of the present invention such as monoclonal antibodies. Furthermore, as for an immunological measuring method, RIA method, ELISA method, fluorescent antibody method, plaque method, spot method, hemagglutination method and Ouchterlony method can be used.

As for transgenic carps having resistance to Koi herpesvirus of the present invention, there is no specific limitation as long as it is a transgenic carp that can be obtained by introducing a gene expression vector of one or more of the proteins of the present invention. When constructing expression vectors that introduce one or more genes of the protein of the present invention to carps, it is preferred to prepare expression vectors wherein the gene of the protein of the present invention is connected in the downstream of the promoter which effectively express the gene in carp cells. As for promoters, β-actine promoter, adipocyteP2 (aP2) promoter, Mylz2 (Danio rerio myosin light polypeptide 2 skeletal muscle mylz2) promoter, UCP promoter, SV40 promoter, cytomegavirus promoter, EF1α promoter, metallothionein promoter or heat shock promoter, can be used. Among these, cyprinodont β-actine promoter or mylz2 promoter is preferable from the point of view of expression efficiency. Further, it is preferable to connect polyadenylation sequence such as bovine growth hormone polyadenylation sequence in the downstream of the gene of the protein of the present invention, in order to stabilize mRNA. Furthermore, intron sequence or enhancer sequence having function to enhance gene expression, or terminator sequence commanding the end of transcription can be used, according to need. Introduction of the constructed expression vector to carps can be performed by microinjection method to oocytes or fertilized eggs, virus vector infection method, particle gun method or electropolating method. Meanwhile, the transgenic carps of the present invention include adult carps, its offspring as well as fertilized egg cells of carp and carp germ cells to which the protein gene of the present invention is introduced, for convenience.

In the following, the present invention will be described in detail by referring to the Examples, but the present invention will not be limited to these Examples.

EXAMPLE 1

Translation initiation codon to translation stop codon of 5 types of glycoprotein genes and 5 types of membrane protein genes coded by the genome of KHV separated in Japan, United States and Israel, on which the present inventors have performed genomic analysis, were amplified by polymerase chain reaction (PCR). The primers used are shown in Table 1. As for template DNAs at the time of PCR, KHV-J separated in Japan was used. PCR condition was 30 sec at 95° C., 30 sec at 55° C., 30 sec at 72° C. ran as 1 cycle, which was repeated for 30 cycles.

TABLE 1

| | | |
|---|---|---|
| KHV-g1-F | SEQ ID NO: 21 | 5'-ATGCCTGCCACCTTTGGCAG-3' |
| KHV-g1-R | SEQ ID NO: 22 | 5'-TCACCCCGCAGAGGTACCAT-3' |
| KHV-g2-F | SEQ ID NO: 23 | 5'-ATGTACCAGCAGCAATACCA-3' |
| KHV-g2-R | SEQ ID NO: 24 | 5'-TCAGTTGTGAAGAGTAGATT-3' |
| KHV-g3-F | SEQ ID NO: 25 | 5'-ATGAGCCACAGACAGCCAGC-3' |
| KHV-g3-R | SEQ ID NO: 26 | 5'-TCAGTAATAGTAATAGTTGT-3' |
| KHV-g4-F | SEQ ID NO: 27 | 5'-ATGCCGTCGAGCATGACTGG-3' |
| KHV-g4-R | SEQ ID NO: 28 | 5'-TCAGAGTTCGTCTCTGATGG-3' |
| KHV-g5-F | SEQ ID NO: 29 | 5'-ATGTCTATGCGCCCGCACAA-3' |
| KHV-g5-R | SEQ ID NO: 30 | 5'-CTACCGAGTGAGCCGTCTCT-3' |

TABLE 1-continued

| | | |
|---|---|---|
| KHV-m1-F | SEQ ID NO: 31 | 5'-ATGACGGAGCGGGCAGCGCT-3' |
| KHV-m1-R | SEQ ID NO: 32 | 5'-TTAGAAGACGAGCAAGCCCT-3' |
| KHV-m1-F | SEQ ID NO: 33 | 5'-ATGTCTCCTTTGTGCGGTCT-3' |
| KHV-m2-R | SEQ ID NO: 34 | 5'-CTATACGCGCTCATAACCCC-3' |
| KHV-m3-F | SEQ ID NO: 35 | 5'-ATGAGCGCGTATAGGTACAA-3' |
| KHV-m3-R | SEQ ID NO: 36 | 5'-TCAGACGAGCTCGTTGAGGA-3' |
| KHV-m4-F | SEQ ID NO: 37 | 5'-ATGGCAGTCACCAAAGCTCA-3' |
| KHV-m4-R | SEQ ID NO: 38 | 5'-TCACCACATCTTGCCGGTGT-3' |
| KHV-m5-F | SEQ ID NO: 39 | 5'-ATGGATGCACCGGTCTTCTC-3' |
| KHV-m5-R | SEQ ID NO: 40 | 5'-TCAGGCGGCTGTCTTCCTCT-3' |

PCR amplified DNA were cloned into gene expression vector pcDNA 3.1, and was introduced into *E. coli*. The transformed *E. coli* was cultured in large amount to extract and purify plasmid DNA. Purification of plasmid was performed by ultracentrifugation by using cesium chloride (Molecular cloning, 3rd Ed.).

EXAMPLE 2

In the vaccine test, 50 μg of DNA per carp was inoculated to the dorsal muscle of a carp with 100 μL of phosphate buffered saline (PBS) by using an injector. At that time, various glycoprotein genes and membrane protein genes were inoculated respectively. As a negative control, vector plasmid DNA alone was inoculated. Carps were raised for 30 days after vaccine inoculation in a circulating filtration tank at 23° C.

In the infection test, branchiae of KHV infected carps were homogenized in PBS, and solution filtered with a 0.22 μm filter were inoculated at 100 μL per carp. After inoculating viral solution, carps were raised in a re-circulating filtration tank at 23° C.

After KHV infection, carps were observed for 12 days, and the accumulated mortality rate of carps was calculated. Results are shown in FIG. 1. As a test result, carps in the control area showed about 50% of accumulated mortality rate, while the accumulated mortality rate of carps in the vaccine test area was, about 13 to 40% for glycoprotein and 14 to 40% for membrane protein. Thus, the effectiveness of infection control by the DNA vaccine against KHV infection, or the vaccine effect was revealed.

EXAMPLE 3

A vaccine test was performed similarly to the above method. 5 types of glycoprotein gene (group 2) and 5 types of membrane protein gene (group 3) were mixed and inoculated, respectively. Vector plasmid DNA alone was used as negative control (group 1). Carps were raised for 30 days after vaccine inoculation in a re-circulating filtration tank at 23° C., and infection experiment was performed similarly to the above description.

After KHV infection, carps were observed for 3 weeks, and the accumulated mortality rate of carps was calculated. Results are shown in FIG. 2. As a test result, carps in the control area showed about 60% of accumulated mortality rate, while the accumulated mortality rate of carps in the vaccine test area was about 10 to 20%. Thus, the effectiveness of infection control by the DNA vaccine against KHV infection or vaccine effect was revealed.

INDUSTRIAL APPLICABILITY

According to the DNA vaccines for carps of the present invention, immunocompetence against Koi herpesvirus disease caused by Koi herpesvirus (KHV) can be conferred. More specifically, according to the DNA vaccine for carps of the present invention, it is possible to induce immune response (including humoral immune response and cellular immune response) against Koi herpesvirus disease, and it is effective for preventing infection of Koi herpesvirus (KHV) or treating Koi herpesvirus disease.

The invention claimed is:

1. A composition comprising, a recombinant vector comprising a DNA encoding a glycoprotein of Koi herpesvirus (KHV) consisting of the amino acid sequence as shown by SEQ ID NO: 2 and a pharmaceutically acceptable carrier.

2. A method for reducing mortality of a carp after being infected with Koi herpesvirus (KHV), by administering the composition of claim 1, wherein the reduction in mortality is in comparison to a carp not receiving said composition.

* * * * *

SEQUENCE LISTING

<160> NUMBER OF SEQ ID NOS: 40

<210> SEQ ID NO 1
<211> LENGTH: 1350
<212> TYPE: DNA
<213> ORGANISM: koi herpesvirus

<400> SEQUENCE: 1

```
atgcctgcca cctttggcag gcgccctgac ggggatgacc aagtgtacct ggaagaggac      60
acggatgacg ggggattcag tggcagagca ccagcaccac cccaggtggc cctggccctg     120
gacctggact taggggacag gcttactcag tttcctcacc actctgctgc agtcaggggt     180
ggcctgagag gctgcctggg caaggtactg agcatctcca ggggcaggct gctgatgggg     240
gtggtgggcc taggcctgct gctggccttc atcgtgttca tggtggagaa gacggactcc     300
aggctgctgg acgaggccaa gtgtccagac caggcccgtg tgtactaccc tctgaggacg     360
cacaggcgca agttcagctt catgttctgc tgccactgct gtgccctcaa gcagccccac     420
atctgctacg aggacatgtt caagtggctt gaccactggt acaacgacac gctgtcccaa     480
gaggagcaga tgggctttgc ccaacatgtg tgggcagccg gcgtggtgag aggccacctg     540
gagcgcaagg ctgctcccct gtctcagcag gaccaggact cttggcctca gaacctgcgc     600
cagatggtca aacgcacgcg ctgggttgag tggctggtgg gggagcacta cgccaagagc     660
ctcaaccaca cgctggctgg tacagaggac tacgagcacc tgagcaagca caccatcttt     720
gacgactccg agcagctcag gcccatcaac agcacgcaca acgtactgc caagacctac     780 aagctggaga ccttggtggt ggacaatgtg tacgcagcgg acgagctggt ggccttcatg     840
gtggagtctg gcacgctca ggacactacc atgttcagga tggccttcaa ccagtactac     900
ggcgcctaca acgtgtacga cgagctgttc cacaaggcgc tggacctcgc cggcgtggtg     960
gactctgtcg cctacatgcc ctctgcggct gaggtgctga tcgaggctgc catggacgag    1020
gccttctcgt acaaccctga cgaggaggat gccaggctca acgcttccag ggccaacgca    1080
accagcaaca gcaccctgat gaacggcacc tgctctctgg agcagctgtg caaggcctat    1140
gatgttgctg cgactaccat gccgtctccc tctgctctcc tcagcaccag tgacgtcaca    1200
acacccagca tcaggcccag gaccagtgac gtcaccgcgc ccagcagcag gaccagtcac    1260
accacgcccc cttctggtac ccatgatggc tccaccgtgt ggactgttgg taacattaca    1320
atgactgcta atggtacctc tgcggggtga                                      1350
```

<210> SEQ ID NO 2
<211> LENGTH: 449
<212> TYPE: PRT
<213> ORGANISM: koi herpesvirus

<400> SEQUENCE: 2

```
Met Pro Ala Thr Phe Gly Arg Arg Pro Asp Gly Asp Gln Val Tyr
1               5                   10                  15

Leu Glu Glu Asp Thr Asp Asp Gly Gly Phe Ser Gly Arg Ala Pro Ala
            20                  25                  30
```

-continued

Pro Pro Gln Val Ala Leu Ala Leu Asp Leu Asp Phe Arg Asp Arg Leu
            35                  40                  45
Thr Gln Phe Pro His His Ser Ala Ala Val Arg Gly Gly Leu Arg Gly
        50                  55                  60
Cys Leu Gly Lys Val Leu Ser Ile Ser Arg Gly Arg Leu Leu Met Gly
65                  70                  75                  80
Val Val Gly Leu Gly Leu Leu Leu Ala Phe Ile Val Phe Met Val Glu
                85                  90                  95
Lys Thr Asp Ser Arg Leu Leu Asp Glu Ala Lys Cys Pro Asp Gln Ala
            100                 105                 110
Arg Val Tyr Tyr Pro Leu Arg Thr His Arg Arg Lys Phe Ser Phe Met
            115                 120                 125
Phe Cys Cys His Cys Cys Ala Leu Lys Gln Pro His Ile Cys Tyr Glu
        130                 135                 140
Asp Met Phe Lys Trp Leu Asp His Trp Tyr Asn Asp Thr Leu Ser Gln
145                 150                 155                 160
Glu Glu Gln Met Gly Phe Ala Gln His Val Trp Ala Ala Gly Val Val
                165                 170                 175
Arg Gly His Leu Glu Arg Lys Ala Ala Pro Leu Ser Gln Gln Asp Gln
            180                 185                 190
Asp Ser Trp Pro Gln Asn Leu Arg Gln Met Val Lys Arg Thr Arg Trp
        195                 200                 205
Val Glu Trp Leu Val Gly Glu His Tyr Ala Lys Ser Leu Asn His Thr
210                 215                 220
Leu Ala Gly Thr Glu Asp Tyr Glu His Leu Ser Lys His Thr Ile Phe
225                 230                 235                 240
Asp Asp Ser Glu Gln Leu Arg Pro Ile Asn Ser Thr His Asn Gly Thr
            245                 250                 255
Ala Lys Thr Tyr Lys Leu Glu Thr Leu Val Val Asp Asn Val Tyr Ala
            260                 265                 270
Ala Asp Glu Leu Val Ala Phe Met Val Glu Ser Gly His Ala Gln Asp
        275                 280                 285
Thr Thr Met Phe Arg Met Ala Phe Asn Gln Tyr Tyr Gly Ala Tyr Asn
    290                 295                 300
Val Tyr Asp Glu Leu Phe His Lys Ala Leu Asp Leu Ala Gly Val Val
305                 310                 315                 320
Asp Ser Val Ala Tyr Met Pro Ser Ala Ala Glu Val Leu Ile Glu Ala
            325                 330                 335
Ala Met Asp Glu Ala Phe Ser Tyr Asn Pro Asp Glu Glu Asp Ala Arg
            340                 345                 350
Leu Asn Ala Ser Arg Ala Asn Ala Thr Ser Asn Ser Thr Leu Met Asn
        355                 360                 365
Gly Thr Cys Ser Leu Glu Gln Leu Cys Lys Ala Tyr Asp Val Ala Ala
    370                 375                 380
Thr Thr Met Pro Ser Pro Ser Ala Leu Leu Ser Thr Ser Asp Val Thr
385                 390                 395                 400
Thr Pro Ser Ile Arg Pro Arg Thr Ser Asp Val Thr Ala Pro Ser Ser
            405                 410                 415
Arg Thr Ser His Thr Thr Pro Pro Ser Gly Thr His Asp Gly Ser Thr
            420                 425                 430
Val Trp Thr Val Gly Asn Ile Thr Met Thr Ala Asn Gly Thr Ser Ala
        435                 440                 445
Gly

```
<210> SEQ ID NO 3
<211> LENGTH: 1518
<212> TYPE: DNA
<213> ORGANISM: koi herpesvirus

<400> SEQUENCE: 3
atgtaccagc agcaatacca gcagacgagg gaccagagga gcctgctgtg tctggggcgg     60
gctcccctca cgctcacgct cgcctcacag cccatcactc gccgcctcgt ggcgtctggt    120
gagtacagca actctcctgc atcagcatca gtacccacag cagcatctgc agcatcagta    180
cccacagcag caccagtacc agtggagtac cagcgccgtc ctgtggctgc actggagtac    240
tgcaacgggg agagtggcgc aagcatcgag agtggacttt cgctgctggc caggcgtcct    300
ctcaagaggg caaggagggc tgctgaggtg gaggctgaag gggctgaagg ggctaaaggg    360
gctgaagggg ccgtagagga agacgctgaa ggggccgtag aggaagacgc tgagggacc    420 gtcgaggagg acactgtcga ggacgaggca gaaatggcgc aagcaccgtt ggtcaagaga    480
aagaggcgca agagacgtgc gtcgtgctgg ggcaccaaga agagaaggac caccgcctct    540
cactctgtgg cagaggactc tgtggcagag gtggcagagg acaccaccac agtgaccgtc    600
gaggaggagg acggcgggga gtcacaaatg gcgcaagcac taattgtgac aatggggcac    660
aacggcgctg agggtactgt ggacactgct gtgaccactt acactgtgga cactgaggac    720
actgctgtgg acattgacac tgtgaccact gctgaggaca ctgatgtggt catggttgac    780
gctgaggagg acactgagga ggacactgag gaggacactg aagtgaccat tgaaaccaat    840
gacaaaggtg ttgtcgaaac ttatggaaaa aacgcaacta cccttggtag tgatgacgaa    900
cagggtggtg acaaacggaa agagggtgca gctgccgttg cgccggggg tgaagattgc    960 gcaaatatcg cgtgtgaaag ggagggggca gtatctgaca aacaaatgtt cccggtacag   1020
tcaccgcaca cacccaaact cctccctct gaatcacgcc aaaggggagt ggtaaccaat   1080
cagaagccaa tttccacaga aggggtgggg ttattgagca ataacgggaa tgactgttcc   1140
caacatactg gtttactggc aaccacgccc cataccggtt tggtttcgtc cacaccccat   1200
atggggtata agaaccctga ctctggagag gttcggcatt ctaccactga cactgccact   1260
gccactgtct ccgttgacac cgtctttgac tctgttaccg ttgatactgt ctttgactct   1320
gttgactccg acgacttgtc gctactcttt gacactttgg tccagcaaaa gactctcgaa   1380
ctcagacaga gactcaagag catctacgaa cacagcacca gcttctgcac tccagacttc   1440
acccagagag cccacagcct cctgctagac tacaaggact tgccctcaa agaactgcaa   1500 tctactcttc acaactga                                                 1518

<210> SEQ ID NO 4
<211> LENGTH: 505
<212> TYPE: PRT
<213> ORGANISM: koi herpesvirus

<400> SEQUENCE: 4

Met Tyr Gln Gln Gln Tyr Gln Gln Thr Arg Asp Gln Arg Ser Leu Leu
  1               5                  10                  15

Cys Leu Gly Arg Ala Pro Leu Thr Leu Thr Leu Ala Ser Gln Pro Ile
             20                  25                  30

Thr Arg Arg Leu Val Ala Ser Gly Glu Tyr Ser Asn Ser Pro Ala Ser
         35                  40                  45

Ala Ser Val Pro Thr Ala Ala Ser Ala Ala Ser Val Pro Thr Ala Ala
     50                  55                  60
```

```
Pro Val Pro Val Glu Tyr Gln Arg Arg Pro Val Ala Leu Glu Tyr
 65                  70                  75                  80

Cys Asn Gly Glu Ser Gly Ala Ser Ile Glu Ser Gly Leu Ser Leu Leu
                 85                  90                  95

Ala Arg Arg Pro Leu Lys Arg Ala Arg Arg Ala Ala Glu Val Glu Ala
            100                 105                 110

Glu Gly Ala Glu Gly Ala Lys Gly Ala Glu Gly Ala Val Glu Glu Asp
            115                 120                 125

Ala Glu Gly Ala Val Glu Glu Asp Ala Glu Gly Thr Val Glu Glu Asp
            130                 135                 140

Thr Val Glu Asp Glu Ala Glu Met Ala Gln Ala Pro Leu Val Lys Arg
145                 150                 155                 160

Lys Arg Arg Lys Arg Arg Ala Ser Cys Trp Gly Thr Lys Lys Arg Arg
                165                 170                 175

Thr Thr Ala Ser His Ser Val Ala Glu Asp Ser Val Ala Glu Val Ala
                180                 185                 190

Glu Asp Thr Thr Thr Val Thr Val Glu Glu Glu Asp Gly Gly Glu Ser
            195                 200                 205

Gln Met Ala Gln Ala Leu Ile Val Thr Met Gly His Asn Gly Ala Glu
210                 215                 220

Gly Thr Val Asp Thr Ala Val Thr Thr Tyr Thr Val Asp Thr Glu Asp
225                 230                 235                 240

Thr Ala Val Asp Ile Asp Thr Val Thr Thr Ala Glu Asp Thr Asp Val
                245                 250                 255

Val Met Val Asp Ala Glu Glu Asp Thr Glu Asp Thr Glu Asp
                260                 265                 270

Thr Glu Val Thr Ile Glu Thr Asn Asp Lys Gly Val Val Glu Thr Tyr
                275                 280                 285

Gly Lys Asn Ala Thr Thr Leu Gly Ser Asp Asp Glu Gln Gly Gly Asp
            290                 295                 300

Lys Arg Lys Glu Gly Ala Ala Val Gly Ala Gly Gly Glu Asp Cys
305                 310                 315                 320

Ala Asn Ile Ala Cys Glu Arg Glu Gly Ala Val Ser Asp Lys Gln Met
                325                 330                 335

Phe Pro Val Gln Ser Pro His Thr Pro Lys Leu Leu Pro Ser Glu Ser
                340                 345                 350

Arg Gln Arg Gly Val Val Thr Asn Gln Lys Pro Ile Ser Thr Glu Gly
                355                 360                 365

Val Gly Leu Leu Ser Asn Asn Gly Asn Asp Cys Ser Gln His Thr Gly
                370                 375                 380

Leu Leu Ala Thr Thr Pro His Thr Gly Leu Val Ser Ser Thr Pro His
385                 390                 395                 400

Met Gly Tyr Lys Asn Pro Asp Ser Gly Glu Val Arg His Ser Thr Thr
                405                 410                 415

Asp Thr Ala Thr Ala Thr Val Ser Val Asp Thr Val Phe Asp Ser Val
                420                 425                 430

Thr Val Asp Thr Val Phe Asp Ser Val Asp Ser Asp Leu Ser Leu
                435                 440                 445

Leu Phe Asp Thr Leu Val Gln Gln Lys Thr Leu Glu Leu Arg Gln Arg
450                 455                 460

Leu Lys Ser Ile Tyr Glu His Ser Thr Ser Phe Cys Thr Pro Asp Phe
465                 470                 475                 480

Thr Gln Arg Ala His Ser Leu Leu Leu Asp Tyr Lys Asp Phe Ala Leu
                485                 490                 495
```

Lys Glu Leu Gln Ser Thr Leu His Asn
            500                 505

<210> SEQ ID NO 5
<211> LENGTH: 4587
<212> TYPE: DNA
<213> ORGANISM: koi herpesvirus

<400> SEQUENCE: 5

| | | | | | |
|---|---|---|---|---|---|
| atgagccaca | gacagccagc | caagagccag | ggccagggcc | agggcaaggg | caagggcaag | 60 |
| ccagccaaga | ggcctgcacc | tgctgcactc | agcgcctttg | actcttctga | tgaggaggag | 120 |
| gataccacca | ccactgttgc | tccaaccaga | cccaagaagc | agcctgccaa | acccaagtcc | 180 |
| aaggaggtcg | tggaggtgtc | ctctgcctcc | tctgtctctg | agtcctctgc | ctcagattct | 240 |
| gagtctgagg | cctcctctgc | ctcctctgcc | tcctctgcct | cctctgcctc | ctctgcctct | 300 |
| tcctctgaat | cctcagcctc | tgattctgac | tctgacaacg | gcggtgacaa | gtacaacaag | 360 |
| gacgagccac | catcctctga | tccagaatct | gaacacgaga | atgcccctgc | accacccatc | 420 |
| aaccgcaaga | tcaaaggcag | aaccgctctg | gcaccctcca | agggcaaggc | caaggccacc | 480 |
| aagaagcagc | cagagtcctc | ctcctcgtcc | tcttctgcat | cctcctcttc | tgcctcttca | 540 |
| gactctgaag | actctgaaga | cgaaccacct | gcacccagaa | ccaaggtaat | gcttgtcaaa | 600 |
| aaagctgctc | ctgctcctgc | taaaactgtt | cctgtgtctg | tacctgtacc | tgcaaaaccc | 660 |
| agcaagactt | ttcctgtgcc | tgtgcctgcc | aagaagacta | cacaaacact | tgaaaaaacc | 720 |
| atccagaaac | caaccactac | tcaaaccccct | caaaaaccca | agactgctcc | tcctgctact | 780 |
| gttcctgttc | ctgccaagac | tgccaagaca | actcaacctc | aacccaaggt | accacagcag | 840 |
| ccaccacctg | ccaagaccaa | taccacatca | aacccaaac | ccaaaaatcc | cgcaagcaca | 900 |
| cagaggagag | tgaccctgga | cgaggaggac | gactcaccct | tgtcaggtc | caagagcagg | 960 |
| acgcctgtga | aggcgccttc | caagtcgcca | cctgctcccc | atgctgcacc | catcactgcc | 1020 |
| aacatccctg | tcattgaaga | gtacgatccc | accctgcctc | agctgcctgc | aggtaagacc | 1080 |
| atttctaaat | cattagcacc | cacacctgtg | cctgtacctg | ttgttgtaga | tgatgttaat | 1140 |
| gataatggta | atgatagtga | cgctaaggct | aatgagactg | agactctgga | tactctaacc | 1200 |
| gctgatatac | ccatgtctga | ctctgaggat | gaggatgaga | ctcaagttga | gattgctgat | 1260 |
| gataaagata | tgatgttaa | ggataatgac | gatgttaatg | atgttgagat | gagagagatg | 1320 |
| cagcagatga | taaactctga | catgatggtc | aggccagtca | gccctctgcc | tgctgatgat | 1380 |
| gcttctgatg | agggatgcca | agcagcctct | cagagcatcc | ttgataatga | taatggtaat | 1440 |
| ggtgatgata | atggtaataa | taatgatgat | gaggaggagg | aggaggagga | ggaggaggag | 1500 |
| gaaatggagc | aagcatcacc | ttcacctgct | ctcgctgtcc | tggccgctat | ggctggagac | 1560 |
| ttaccatgca | ctgctcaacc | tgagcctcag | ccagagccag | aaccagaacc | agagcctcag | 1620 |
| cctcagcctc | agcctcccaa | acagcagcct | ctagactttt | tgacttctct | gatctgcctc | 1680 |
| acatccaaac | cctccatcac | agtctgtgag | gcagaggcgg | tcactgcttc | tatcaatgca | 1740 |
| gacaactcta | aaaatggtgc | aagcacaggt | gtgagtgata | atgttttttg | caatcctgag | 1800 |
| cctcctgcat | cacccacttc | agtcacacca | ccaccacctg | ccaccatggt | ctctatgatc | 1860 |
| atcccaggct | tgggtgacat | agaagaaatg | attgttgtag | acactgctgc | tgatgctgat | 1920 |
| gctgatgctg | atgctgatgc | tgatgctgat | aatggtgagg | atgagactga | agtggctgat | 1980 |
| gtgctggagc | tcagtgctgg | gcaagagttt | gagcccttgg | aacctgcaag | cagcaagacg | 2040 |

```
cctaaaaccc ctaaagaaat aaagaaacct gagcagccca agccaagaac ccataaagac    2100
agagacacca gagacaccag agagagagag cagagagagg aacaggtggt gagacccaaa    2160
gaacgtagag aaaaggacaa gaaggagaga gagagggagg agaggagaag ggagaaatcg    2220
agcaaacaca gcagcaggtg cacgatggtg tgtgagactg tggcagagac tgccacgccg    2280
cctccaagcc gtcgctcacc caacatgccc acttcatcac ccacaactac tcccgcaacg    2340
gtgcagtctg tggtggtgca gcccacaccc tcaccctcag cctctcacag accctccaag    2400
gccaagcagc agcaagagga cctcaagcag agtgctgaag cggccagact tgccatgatg    2460
gagagggaga gggagagacg tcgcagagac agacagaggg ctgatgcaga cgccgaggtt    2520
gccgcactca gagacgtggc ccttgaaaga cgcagacaag agagacagcg cgaggctgag    2580
gagctggagg aggctgcact cagagacgtc gcactcgccg ccaagcaaaa aggtaagaca    2640
aagagcacca gcagcaagac gcctgaaact cagcaaaacg ttgcagctgt tccagtcact    2700
ccaacaaccc ttcaaaacac tcacacttct tctccctctt ctgcagcagc acagcggcca    2760
agaacagact cttctgcagc cagcagcaaa gactcaagca aagacaccaa gaaggacaag    2820
aaggccacca agagagagag gtgcagggag gatgagactc catcctccag acgcagagac    2880
aggtctccca caccaccacc aagagaagg tcacctgcac cctcttcttc ttcacactct    2940
cactcacact cacagcagca gcagcctcag cccatcatgc cacagggtca gaggatgtcc    3000
tacgatgagc agctcagcat cctcaagcag gtcaaggata gagtcatgca ggcgtctgcc    3060
aagctgcccg cactgacttc tgtagactac aacctgagaa tggctgccct gagcgagtgt    3120
aggaagaaca gcctggccgt ctttgtgaat gccctgcaag tgtgtggagc tgagacgctc    3180
tggaactcta gggctgccct ccaagcctcc atcatgcaag accaagaagt tgaaccccta    3240
ccagcctccg tggtcactct gcacatcatc atgcagcacg ccttcaacaa gcacgagttc    3300
acactgtgcg ccaagttcct accagtggtg aacagcctcc tgaccaggat gtccccagca    3360
gacgttgtgt cctacatgat ggccagagag cgcaaaaaca ggggagatga tgtgcacgag    3420
acgtctgacc ccatgcagtt tgagtctccc attgagaggg agctgtctga ggcctccagt    3480
accctgctgt gcgaactgta ccacgcaaac ctctctggct acaggcagca caccgccacc    3540
atgtatccct ggctgctcaa gtgcctgaac ggcatcctgg actctgtgta cggcaaggct    3600
ggtggcactg cagccatggc tgctgacctc ttggtggccc tgcagaaatc acccgagctg    3660
cccgccactg atggtgccgt cattggcgca agcaccacgt ccatggaggt gactgtgatg    3720
gagatgattg gggtcatcat ggctgcaaga cacaggagg ccaagctcct ggccgagatt    3780
gtgtccatgg actttacagg tacagactgg gccaagttca ccactctgtc ttccctgcag    3840
ctgctgcact acgcctccat ggtgcaggtc tggggcaaca accctccaga ggtgctgatg    3900
gtcagagaag agcccctgag atggatgttt gcagtcaaga accgcaagct gccctacact    3960
ccgtttgtac cctccatcac ctctctggtc tgcaccctca ggtggctaca ctccttcaga    4020
cccaggagat gcctgactgc agtcactgag cactatgtca atcagcacaa ggctgtggag    4080
aggggagaca tgaccgctga cgaggtcaag atgtggcgtc tggacgatga ctttagcggt    4140
gaggtgaggt ctgtggccct gagaaacgtg tcctacctct gcacccagaa acccttgcc    4200 actggctcct cacacgctgt cagggcagag attgaacccc tggtggaaga cctcagagtc    4260
cagcagagaa ccactgcctc caaggtacca cgcaagtctg cactcaagac acctgaaccc    4320
accactgcca ccgctgcagc caccacagga ggagactctt ctgatgatga gcagcctcag    4380
cagcagcaga ggggaaggag agtgagggtc agcgcaccca gctccagaag aagcagcaga    4440
```

-continued

```
gtgaggtcca ggtccaggtc cagagtggac tctgactctg atgatggcct gtccacacgc    4500
agcggagcca gcagcttctc ctctagaagg tacagtttaa tccattatgt ttttttata     4560 caatgttaca actattacta ttactga                                        4587
```

<210> SEQ ID NO 6
<211> LENGTH: 1528
<212> TYPE: PRT
<213> ORGANISM: koi herpesvirus

<400> SEQUENCE: 6

```
Met Ser His Arg Gln Pro Ala Lys Ser Gln Gly Gln Gly Gln Gly Lys
 1               5                  10                  15

Gly Lys Gly Lys Pro Ala Lys Arg Pro Ala Pro Ala Ala Leu Ser Ala
            20                  25                  30

Phe Asp Ser Ser Asp Glu Glu Glu Asp Thr Thr Thr Val Ala Pro
        35                  40                  45

Thr Arg Pro Lys Lys Gln Pro Ala Lys Pro Lys Ser Lys Glu Val Val
 50                  55                  60

Glu Val Ser Ser Ala Ser Ser Val Ser Glu Ser Ser Ala Ser Asp Ser
 65                  70                  75                  80

Glu Ser Glu Ala Ser Ser Ala Ser Ser Ala Ser Ser Ala Ser Ser Ala
                85                  90                  95

Ser Ser Ala Ser Ser Ser Glu Ser Ala Ser Asp Ser Asp Ser Asp
            100                 105                 110

Asn Gly Gly Asp Lys Tyr Asn Lys Asp Glu Pro Pro Ser Ser Asp Pro
        115                 120                 125

Glu Ser Glu His Glu Asn Ala Pro Ala Pro Ile Asn Arg Lys Ile
130                 135                 140

Lys Gly Arg Thr Ala Leu Ala Pro Ser Lys Gly Lys Ala Lys Ala Thr
145                 150                 155                 160

Lys Lys Gln Pro Glu Ser Ser Ser Ser Ser Ala Ser Ser Ser
                165                 170                 175

Ser Ala Ser Ser Asp Ser Glu Asp Ser Glu Asp Glu Pro Pro Ala Pro
            180                 185                 190

Arg Thr Lys Val Met Leu Val Lys Lys Ala Ala Pro Ala Pro Ala Lys
        195                 200                 205

Thr Val Pro Val Ser Val Pro Val Ala Lys Pro Ser Lys Thr Val
    210                 215                 220

Pro Val Pro Val Pro Ala Lys Lys Thr Thr Gln Thr Leu Glu Lys Thr
225                 230                 235                 240

Ile Gln Lys Pro Thr Thr Thr Gln Thr Pro Gln Lys Pro Lys Thr Ala
                245                 250                 255

Pro Pro Ala Thr Val Pro Val Pro Ala Lys Thr Ala Lys Thr Thr Gln
            260                 265                 270

Pro Gln Pro Lys Val Pro Gln Gln Pro Pro Ala Lys Thr Asn Thr
        275                 280                 285

Thr Ser Gln Pro Lys Pro Lys Asn Pro Ala Ser Thr Gln Arg Arg Val
    290                 295                 300

Thr Leu Asp Glu Glu Asp Asp Ser Pro Phe Val Arg Ser Lys Ser Arg
305                 310                 315                 320

Thr Pro Val Lys Ala Pro Ser Lys Ser Pro Ala Pro His Ala Ala
                325                 330                 335

Pro Ile Thr Ala Asn Ile Pro Val Ile Glu Glu Tyr Asp Pro Thr Leu
            340                 345                 350
```

```
Pro Gln Leu Pro Ala Gly Lys Thr Ile Ser Lys Ser Leu Ala Pro Thr
        355                 360                 365
Pro Val Pro Val Pro Val Val Asp Asp Val Asn Asp Asn Gly Asn
370                 375                 380
Asp Ser Asp Ala Lys Ala Asn Glu Thr Glu Thr Leu Asp Thr Leu Thr
385                 390                 395                 400
Ala Asp Ile Pro Met Ser Asp Ser Glu Asp Glu Asp Glu Thr Gln Val
                405                 410                 415
Glu Ile Ala Asp Asp Lys Asp Asn Asp Val Lys Asp Asn Asp Asp Val
                420                 425                 430
Asn Asp Val Glu Met Arg Glu Met Gln Gln Met Ile Asn Ser Asp Met
            435                 440                 445
Met Val Arg Pro Val Ser Pro Leu Pro Ala Asp Asp Ala Ser Asp Glu
        450                 455                 460
Gly Cys Gln Ala Ala Ser Gln Ser Ile Leu Asp Asn Asp Asn Gly Asn
465                 470                 475                 480
Gly Asp Asp Asn Gly Asn Asn Asn Asp Glu Glu Glu Glu Glu
                485                 490                 495
Glu Glu Glu Glu Glu Met Glu Gln Ala Ser Pro Ser Pro Ala Leu Ala
                500                 505                 510
Val Leu Ala Ala Met Ala Gly Asp Leu Pro Cys Thr Ala Gln Pro Glu
        515                 520                 525
Pro Gln Pro Glu Pro Glu Pro Glu Pro Glu Pro Gln Pro Gln Pro Gln
        530                 535                 540
Pro Pro Lys Gln Gln Pro Leu Asp Phe Leu Thr Ser Leu Ile Cys Leu
545                 550                 555                 560
Thr Ser Lys Pro Ser Ile Thr Val Cys Glu Ala Glu Ala Val Thr Ala
                565                 570                 575
Ser Ile Asn Ala Asp Asn Ser Lys Asn Gly Ala Ser Thr Gly Val Ser
            580                 585                 590
Asp Asn Val Phe Cys Asn Pro Glu Pro Pro Ala Ser Pro Thr Ser Val
        595                 600                 605
Thr Pro Pro Pro Ala Thr Met Val Ser Met Ile Ile Pro Gly Leu
        610                 615                 620
Gly Asp Ile Glu Glu Met Ile Val Val Asp Thr Ala Ala Asp Ala Asp
625                 630                 635                 640
Ala Asp Ala Asp Ala Asp Ala Asp Ala Asp Asn Gly Glu Asp Glu Thr
                645                 650                 655
Glu Val Ala Asp Val Leu Glu Leu Ser Ala Gly Gln Glu Phe Glu Pro
                660                 665                 670
Leu Glu Pro Ala Ser Ser Lys Thr Pro Lys Thr Pro Lys Glu Ile Lys
            675                 680                 685
Lys Pro Glu Gln Pro Lys Pro Arg Thr His Lys Asp Arg Asp Thr Arg
        690                 695                 700
Asp Thr Arg Glu Arg Glu Gln Arg Glu Gln Val Val Arg Pro Lys
705                 710                 715                 720
Glu Arg Arg Glu Lys Asp Lys Lys Glu Arg Glu Glu Arg Arg
                725                 730                 735
Arg Glu Lys Ser Ser Lys His Ser Ser Arg Cys Thr Met Val Cys Glu
            740                 745                 750
Thr Val Ala Glu Thr Ala Thr Pro Pro Pro Ser Arg Arg Ser Pro Asn
        755                 760                 765
Met Pro Thr Ser Ser Pro Thr Thr Pro Ala Thr Val Gln Ser Val
770                 775                 780
```

```
Val Val Gln Pro Thr Pro Ser Pro Ser Ala Ser His Arg Pro Ser Lys
785                 790             795                 800

Ala Lys Gln Gln Gln Glu Asp Leu Lys Gln Ser Ala Glu Ala Ala Arg
            805             810              815

Leu Ala Met Met Glu Arg Glu Arg Arg Arg Arg Asp Arg Gln
            820             825             830

Arg Ala Asp Ala Asp Ala Glu Val Ala Ala Leu Arg Asp Val Ala Leu
            835             840             845

Glu Arg Arg Arg Gln Glu Arg Gln Arg Glu Ala Glu Glu Leu Glu Glu
    850             855             860

Ala Ala Leu Arg Asp Val Ala Leu Ala Ala Lys Gln Lys Gly Lys Thr
865             870             875             880

Lys Ser Thr Ser Ser Lys Thr Pro Glu Thr Gln Gln Asn Val Ala Ala
                885             890             895

Val Pro Val Thr Pro Thr Thr Leu Gln Asn Thr His Thr Ser Ser Pro
            900             905             910

Ser Ser Ala Ala Ala Gln Arg Pro Arg Thr Asp Ser Ser Ala Ala Ser
            915             920             925

Ser Lys Asp Ser Ser Lys Asp Thr Lys Lys Asp Lys Lys Ala Thr Lys
            930             935             940

Arg Glu Arg Cys Arg Glu Asp Glu Thr Pro Ser Ser Arg Arg Arg Asp
945             950             955             960

Arg Ser Pro Thr Pro Pro Lys Arg Arg Ser Pro Ala Pro Ser Ser
            965             970             975

Ser Ser His Ser His Ser His Ser Gln Gln Gln Pro Gln Pro Ile
            980             985             990

Met Pro Gln Gly Gln Arg Met Ser Tyr Asp Glu Gln Leu Ser Ile Leu
            995             1000            1005

Lys Gln Val Lys Asp Arg Val Met Gln Ala Ser Ala Lys Leu Pro
    1010            1015            1020

Ala Leu Thr Ser Val Asp Tyr Asn Leu Arg Met Ala Ala Leu Ser
    1025            1030            1035

Glu Cys Arg Lys Asn Ser Leu Ala Val Phe Val Asn Ala Leu Gln
    1040            1045            1050

Val Cys Gly Ala Glu Thr Leu Trp Asn Ser Arg Ala Ala Leu Gln
    1055            1060            1065

Ala Ser Ile Met Gln Asp Gln Glu Val Glu Pro Leu Pro Ala Ser
    1070            1075            1080

Val Val Thr Leu His Ile Ile Met Gln His Ala Phe Asn Lys His
    1085            1090            1095

Glu Phe Thr Leu Cys Ala Lys Phe Leu Pro Val Val Asn Ser Leu
    1100            1105            1110

Leu Thr Arg Met Ser Pro Ala Asp Val Val Ser Tyr Met Met Ala
    1115            1120            1125

Arg Glu Arg Lys Asn Arg Gly Asp Asp Val His Glu Thr Ser Asp
    1130            1135            1140

Pro Met Gln Phe Glu Ser Pro Ile Glu Arg Glu Leu Ser Glu Ala
    1145            1150            1155

Ser Ser Thr Leu Leu Cys Glu Leu Tyr His Ala Asn Leu Ser Gly
    1160            1165            1170

Tyr Arg Gln His Thr Ala Thr Met Tyr Pro Trp Leu Leu Lys Cys
    1175            1180            1185

Leu Asn Gly Ile Leu Asp Ser Val Tyr Gly Lys Ala Gly Gly Thr
```

| | | | | | | | | | | | |
|---|---|---|---|---|---|---|---|---|---|---|---|
| | | 1190 | | | | 1195 | | | | 1200 | |

Ala Ala Met Ala Ala Asp Leu Leu Val Ala Leu Gln Lys Ser Pro
1205                1210                1215

Glu Leu Pro Ala Thr Asp Gly Ala Val Ile Gly Ala Ser Thr Thr
1220                1225                1230

Ser Met Glu Val Thr Val Met Glu Met Ile Gly Val Ile Met Ala
1235                1240                1245

Ala Arg His Arg Glu Ala Lys Leu Leu Ala Glu Ile Val Ser Met
1250                1255                1260

Asp Phe Thr Gly Thr Asp Trp Ala Lys Phe Thr Thr Leu Ser Ser
1265                1270                1275

Leu Gln Leu Leu His Tyr Ala Ser Met Val Gln Val Trp Gly Asn
1280                1285                1290

Asn Pro Pro Glu Val Leu Met Val Arg Glu Glu Pro Leu Arg Trp
1295                1300                1305

Met Phe Ala Val Lys Asn Arg Lys Leu Pro Tyr Thr Pro Phe Val
1310                1315                1320

Pro Ser Ile Thr Ser Leu Val Cys Thr Leu Arg Trp Leu His Ser
1325                1330                1335

Phe Arg Pro Arg Arg Cys Leu Thr Ala Val Thr Glu His Tyr Val
1340                1345                1350

Asn Gln His Lys Ala Val Glu Arg Gly Asp Met Thr Ala Asp Glu
1355                1360                1365

Val Lys Met Trp Arg Leu Asp Asp Asp Phe Ser Gly Glu Val Arg
1370                1375                1380

Ser Val Ala Leu Arg Asn Val Ser Tyr Leu Cys Thr Gln Lys Pro
1385                1390                1395

Phe Ala Thr Gly Ser Ser His Ala Val Arg Ala Glu Ile Glu Pro
1400                1405                1410

Leu Val Glu Asp Leu Arg Val Gln Gln Arg Thr Thr Ala Ser Lys
1415                1420                1425

Val Pro Arg Lys Ser Ala Leu Lys Thr Pro Glu Pro Thr Thr Ala
1430                1435                1440

Thr Ala Ala Thr Thr Gly Gly Asp Ser Ser Asp Asp Glu Gln
1445                1450                1455

Pro Gln Gln Gln Arg Gly Arg Arg Val Arg Val Ser Ala Pro
1460                1465                1470

Ser Ser Arg Arg Ser Ser Arg Val Arg Ser Arg Ser Arg
1475                1480                1485

Val Asp Ser Asp Ser Asp Gly Leu Ser Thr Arg Ser Gly Ala
1490                1495                1500

Ser Ser Phe Ser Ser Arg Arg Tyr Ser Leu Ile His Tyr Val Phe
1505                1510                1515

Phe Ile Gln Cys Tyr Asn Tyr Tyr Tyr Tyr
1520                1525

<210> SEQ ID NO 7
<211> LENGTH: 1053
<212> TYPE: DNA
<213> ORGANISM: koi herpesvirus

<400> SEQUENCE: 7
atgccgtcga gcatgactgg ctcatggtca tcatcatctc tgcggggtcg acgctctgcg      60
gcatcctcgt cgccgtcgcc gccgccatgt ggatcctcaa caggagcgtg ccctacaaga     120

```
acttcaaata acttccctc aacatgtgca agaacttcaa aactttcccc tctctcctct    180
cctactctcc agccctctct accctcttcg gcctcttcaa tcctcgcccc tctcatcgcc    240
tctcactctc ctctcccctc ttcacaacct cgaaccatgg cagcagcagc gattgcggtg    300
ctcatcctcg cgacggcgac agcggcggcg actagatccc tagaggatac cttcgagggc    360
tcagactggt ccctcacccc ggccgagctg cacaggcccc agatggtggc cctgcaccgc    420
acagggttcc ccttcacagt caagcacggc ggcgccgagt ccaccacctg ccagtgcggc    480
agccccgagc gaccgctcga cggcttcacc cgcagcggcg tccacctcgc cctgcgcttc    540
ttcaacctca cgcaccacca gctcttcgac tacgaccacg tcagggacca gaacgagctc    600
aggtgctcgg acgtgagggg agaggactcg gcccatcacg attttctctg tctctcggcc    660
cagaggtggc ccgcgtgcga gtgcctcatg atcgccaggg agagcctcac cagacccagc    720
cagtaccctc acgacgtcgt cctctcgcac ccctacgacg acatggactg cgacgctgg    780
acgctgcctg ccagagacat cgtccccgag gcctggaagg acatcgagga tcacttcttc    840
cagacagacg tgacccacac cgacaagagg ggagagtgga tgctcttcac cgctcacacc    900
gtcgtcgacc acgcgtcga gggacaccac atcaaagaac acgtccggag agagggcctc    960
tcgcgcgtga ggaaactcgt cgcgcagcac ctcgtaccca atcctcatt cgcgcagtac   1020
cctcgagtag aaaccatcag agacgaactc tga                               1053

<210> SEQ ID NO 8
<211> LENGTH: 350
<212> TYPE: PRT
<213> ORGANISM: koi herpesvirus

<400> SEQUENCE: 8

Met Pro Ser Ser Met Thr Gly Ser Trp Ser Ser Ser Leu Arg Gly
1               5                   10                  15

Arg Arg Ser Ala Ala Ser Ser Pro Ser Pro Pro Cys Gly Ser
            20                  25                  30

Ser Thr Gly Ala Cys Pro Thr Arg Thr Ser Asn Asn Phe Pro Ser Thr
            35                  40                  45

Cys Ala Arg Thr Ser Lys Leu Ser Pro Leu Ser Ser Pro Thr Leu Gln
        50                  55                  60

Pro Ser Leu Pro Ser Ser Ala Ser Ile Leu Ala Pro Leu Ile Ala
65                  70                  75                  80

Ser His Ser Pro Leu Pro Ser Ser Gln Pro Arg Thr Met Ala Ala Ala
                85                  90                  95

Ala Ile Ala Val Leu Ile Leu Ala Thr Ala Thr Ala Ala Thr Arg
            100                 105                 110

Ser Leu Glu Asp Thr Phe Glu Gly Ser Asp Trp Ser Leu Thr Pro Ala
            115                 120                 125

Glu Leu His Arg Pro Gln Met Val Ala Leu His Arg Thr Gly Phe Pro
        130                 135                 140

Phe Thr Val Lys His Gly Gly Ala Glu Ser Thr Thr Cys Gln Cys Gly
145                 150                 155                 160

Ser Pro Glu Arg Pro Leu Asp Gly Phe Thr Arg Ser Gly Val His Leu
                165                 170                 175

Ala Leu Arg Phe Phe Asn Leu Thr His His Gln Leu Phe Asp Tyr Asp
            180                 185                 190

His Val Arg Asp Gln Asn Glu Leu Arg Cys Ser Asp Val Arg Gly Glu
        195                 200                 205

Asp Ser Ala His His Asp Phe Leu Cys Leu Ser Ala Gln Arg Trp Pro
```

```
            210                 215                 220
Ala Cys Glu Cys Leu Met Ile Ala Arg Glu Ser Leu Thr Arg Pro Ser
225                 230                 235                 240

Gln Tyr Pro His Asp Val Val Leu Ser His Pro Tyr Asp Met Asp
            245                 250                 255

Trp Arg Arg Trp Thr Leu Pro Ala Arg Asp Ile Val Pro Glu Ala Trp
                260                 265                 270

Lys Asp Ile Glu Asp His Phe Phe Gln Thr Asp Val Thr His Thr Asp
            275                 280                 285

Lys Arg Gly Glu Trp Met Leu Phe Thr Ala His Thr Val Val Asp His
        290                 295                 300

Gly Val Glu Gly His His Ile Lys Glu His Val Arg Arg Glu Gly Leu
305                 310                 315                 320

Ser Arg Val Arg Lys Leu Val Ala Gln His Leu Val Pro Lys Ser Ser
                325                 330                 335

Phe Ala Gln Tyr Pro Arg Val Glu Thr Ile Arg Asp Glu Leu
            340                 345                 350

<210> SEQ ID NO 9
<211> LENGTH: 699
<212> TYPE: DNA
<213> ORGANISM: koi herpesvirus

<400> SEQUENCE: 9
atgtctatgc gcccgcacaa caggcaatgg gacgcggggt gccgatcgat ttgcttcagc    60
gtcagttgga tattctcaag gagggccaga gtcagcccca gaacagccag cagcagctgc   120
tcgcccagct ccagaagcag ctcgctcaac tccagcaaca gcagcagcag tggtagtcct   180
ctcacccccc cccccttga ccttcaccct tcaccctaa ccccaacaac caaccatgtc     240
ttcatccgcg acggcgttca gcacctcggt ctacgccggg acgttatga tgaccccggt    300 ggccgtcagc gtggtggcgc tcacgctcag cgccgtcacc ttcatcatca tgctgatggc   360
catcgccatg cagcgctacc aactgtgcga ggacgacggc tgcaagaact cgccaagaa    420 ccagtacagg atggacatgc gtcgcaacaa gatgggctac cccggaggag gcggtggtgc   480
gggaggctgc tacgacaacc agtgcttcat ggagaacgag aatcccttca gcgcgccgcc   540
accgccagcc tacaccatgg gccagctgca ctctcgcgga ggacccttga tgatgggccc   600
cctgacggcc gctccgccag catcatcctc gacgcagaac gcataaaagg gctggtggcg   660
cccgcacgac ccgggtcaga gagacggctc actcggtag                          699

<210> SEQ ID NO 10
<211> LENGTH: 232
<212> TYPE: PRT
<213> ORGANISM: koi herpesvirus

<400> SEQUENCE: 10

Met Ser Met Arg Pro His Asn Arg Gln Trp Asp Ala Gly Cys Arg Ser
1               5                   10                  15

Ile Cys Phe Ser Val Ser Trp Ile Phe Ser Arg Arg Ala Arg Val Ser
            20                  25                  30

Pro Arg Thr Ala Ser Ser Ser Cys Ser Pro Ser Ser Arg Ser Ser Ser
        35                  40                  45

Leu Asn Ser Ser Asn Ser Ser Ser Gly Ser Pro Leu Thr Pro Pro
    50                  55                  60

Pro Leu Asp Leu His Pro Ser Pro Leu Thr Pro Thr Thr Asn His Val
65                  70                  75                  80
```

```
Phe Ile Arg Asp Gly Val Gln His Leu Gly Leu Arg Arg Gly Arg Tyr
                85                  90                  95

Asp Asp Pro Gly Gly Arg Gln Arg Gly Gly Ala His Ala Gln Arg Arg
            100                 105                 110

His Leu His His His Ala Asp Gly His Arg His Ala Ala Leu Pro Thr
        115                 120                 125

Val Arg Gly Arg Arg Leu Gln Glu Leu Arg Gln Glu Pro Val Gln Asp
    130                 135                 140

Gly His Ala Ser Gln Gln Asp Gly Leu Pro Arg Arg Arg Arg Trp Cys
145                 150                 155                 160

Gly Arg Leu Leu Arg Gln Pro Val Leu His Gly Arg Glu Arg Ser Leu
                165                 170                 175

Gln Arg Ala Ala Thr Ala Ser Leu His His Gly Pro Ala Ala Leu Ser
            180                 185                 190

Arg Arg Thr Leu Asp Asp Gly Pro Pro Asp Gly Arg Ser Ala Ser Ile
        195                 200                 205

Ile Leu Asp Ala Glu Arg Ile Lys Gly Leu Val Ala Pro Ala Arg Pro
    210                 215                 220

Gly Ser Glu Arg Arg Leu Thr Arg
225                 230

<210> SEQ ID NO 11
<211> LENGTH: 2301
<212> TYPE: DNA
<213> ORGANISM: koi herpesvirus

<400> SEQUENCE: 11
atgacggagc gggcagcgct taacgcgcgc ttcaacccga cggtcacccc gctcagggtg      60
tccacgcaga tcgggagcaa cgtgaagggc aacaacatgc agcagcagcc cctgctcaac     120
tcgggcagaa agctcttttc gaactatcac tacgactata gcggctgcca caacctctct     180
ctccacggcg gcaaccaaca tcatcgcacc gactacgaag acgctcgaca gtaccaccgc     240
cgctaccacg atcaccctct gaacgccaac aggtaccccg tcgccatcgt ctcgcgcaac     300
aaccaccacc acagggtcag ggacaggtcc aggtccccca tccgtcccgc tgcactcaa     360 ccccccggctc agcctcccaa tcagcccaat cagcccccgg ctcagcctcc caatcagccc     420
aatcagcccc cggctcagtc tcccgctcag ccccagagga ctcctcaacc cctgccgccg     480
ccaccgccgc ccgctcagcc ccggcaccag ccgctcaacc tgacggggat gttgcccagg     540
tccgatagga tgtttgacag ctacgacgag acgctcacgc cggctgtcga atcccagac     600 gacagcaaga tgttccccaa ggactttgtc aaggtgatgg tcaacgccag ccgccgcgtg     660
ccgcccgagc cgaccttcac cccggacgac aagttcctcg aggagctctt ccacgccgtc     720
gccagagaag acctcgacgc actcgataag ctggccctcg cgggcacggc caacacggac     780
atgaccacca tccccgtcga tatcaaggac gcggtgcaaa agtacggcct ggccgtcacc     840
aacggcagat ggcccaccag gcagtgcatc gtgagcgccg cgctggcgat cgcaagggc     900 ttctcggcct cgtgcacccc atacaacccc tacacactgg tcaacaccgt gtccttcgtg     960
gaccagcacc cggccagcct ccgcatcggc gtcggcgtcc cgcgcgccga ctacaacgac    1020
gcctggtact cgacgagca ggtgacggga tgctgcgggg acgccaagat gattgcagag    1080
cgccgcgccg tcgcctacca gaagctgccg ggcccagcg cggtgcgcgc cgtgctcgag    1140
gcggacctgc cgtacgtgag gtgcaagctg cccgacgatt ctccgagga cctcaacctc    1200 gactacatct acgacgagca ccaggacggc agcatctttc ccggactgca ctctttccag    1260
```

```
ggcgccttcc agaacgccag gcgcatctgc gccggggtgc ccctggtcat ccactgcaag    1320
aaggtgacgg ggttgctgca gcgggcggac gccatgtacg cgacgctcgc cgccgaggcc    1380
gggtacaccg tggacatctc caagatcaac gaggtggaca cggcctacgc gtcctcggtg    1440
ggcaccctcg cgccctgcgt ggagctgatg gccgccgcca aaaagtacgc cgtcgcgaga    1500
gagaggaagc ccgcgcagat gatcctgggc gccgtcgggg gacccaatgc agacagcgcg    1560
gccttctacg agggcatggc cctctccaac atcgacgagg agttcctcaa gaagatgtgc    1620
gccgtcgcct ccatcaagta cgacatgctc atggagaaga cgttcccctt cgccgcccca    1680
gacaccaaga tccgccaggc ctacgcgttc gccttcaaga tcatagacct catcctgcag    1740
atgctcacgg tcccctggg ttacaagagc gtgcccacgg accaggccga gctggcgctg    1800
aggaccaagc tcgtgcgaca gctgcacacc gccgacctct ttggccgcct gatgtggaag    1860
ctgaacccga ccaagctcga cagggtcaag gccaaggtcg tcaagctcag cgacccgacc    1920
aagcgctggg ccgacaacaa ggcgctctac gccaagttcg acaacctcgg ggaccacatc    1980
aacaccatgc tgctgtccgt caagggcgta cagctctact ttgacacggg caccaccgtc    2040
aacgtgccga ccgagaccgg cgtggagagg gccgcggcgc tgctcgccgc ccgcaagacc    2100
aacaaccacg cgcactttgc cgtgtgccac ctcaaggccc aggccggtct caactcggcc    2160
accgccgaca acgaacccct gttcaggag gactacaagc gcacagacac ccgacccaac    2220
gaggtggtga tgcccagctc cgccgacacc aaccagttcg tgcaggccat caccaagctc    2280
aagggcaagc tcgtcttcta a                                              2301

<210> SEQ ID NO 12
<211> LENGTH: 766
<212> TYPE: PRT
<213> ORGANISM: koi herpesvirus

<400> SEQUENCE: 12

Met Thr Glu Arg Ala Ala Leu Asn Ala Arg Phe Asn Pro Thr Val Thr
1               5                   10                  15

Pro Leu Arg Val Ser Thr Gln Ile Gly Ser Asn Val Lys Gly Asn Asn
            20                  25                  30

Met Gln Gln Gln Pro Leu Leu Asn Ser Gly Arg Lys Leu Phe Ser Asn
        35                  40                  45

Tyr His Tyr Asp Tyr Lys Arg Leu Pro Asn Leu Ser Leu His Gly Gly
    50                  55                  60

Asn Gln His His Arg Thr Asp Tyr Glu Asp Ala Arg Gln Tyr His Arg
65                  70                  75                  80

Arg Tyr His Asp His Pro Leu Asn Ala Asn Arg Tyr Pro Val Ala Ile
                85                  90                  95

Val Ser Arg Asn Asn His His His Arg Val Arg Asp Arg Ser Arg Ser
            100                 105                 110

Pro Ile Arg Pro Ala Arg Thr Gln Pro Pro Ala Gln Pro Asn Gln
        115                 120                 125

Pro Asn Gln Pro Pro Ala Gln Pro Pro Asn Gln Pro Asn Gln Pro
    130                 135                 140

Ala Gln Ser Pro Ala Gln Pro Gln Arg Thr Pro Gln Pro Leu Pro Pro
145                 150                 155                 160

Pro Pro Pro Pro Ala Gln Pro Arg His Gln Pro Leu Asn Leu Thr Gly
                165                 170                 175

Met Leu Pro Arg Ser Asp Arg Met Phe Asp Ser Tyr Asp Glu Thr Leu
            180                 185                 190
```

```
Thr Pro Ala Val Glu Ile Pro Asp Asp Ser Lys Met Phe Pro Lys Asp
            195                 200                 205

Phe Val Lys Val Met Val Asn Ala Ser Arg Arg Val Pro Pro Glu Pro
            210                 215                 220

Thr Phe Thr Pro Asp Asp Lys Phe Leu Glu Leu Phe His Ala Val
225                 230                 235                 240

Ala Arg Glu Asp Leu Asp Ala Leu Asp Lys Leu Ala Leu Ala Gly Thr
                245                 250                 255

Ala Asn Thr Asp Met Thr Thr Ile Pro Val Asp Ile Lys Asp Ala Val
                260                 265                 270

Gln Lys Tyr Gly Leu Ala Val Thr Asn Gly Arg Trp Pro Thr Arg Gln
            275                 280                 285

Cys Ile Val Ser Ala Ala Leu Ala Met Arg Lys Gly Phe Ser Ala Ser
            290                 295                 300

Cys Thr Pro Tyr Asn Pro Tyr Thr Leu Val Asn Thr Val Ser Phe Val
305                 310                 315                 320

Asp Gln His Pro Ala Ser Leu Arg Ile Gly Val Gly Val Pro Arg Ala
                325                 330                 335

Asp Tyr Asn Asp Ala Trp Tyr Cys Asp Glu Gln Val Thr Gly Cys Cys
                340                 345                 350

Gly Asp Ala Lys Met Ile Ala Glu Arg Arg Ala Val Ala Tyr Gln Lys
                355                 360                 365

Leu Pro Gly Pro Ser Ala Val Arg Ala Val Leu Glu Ala Asp Leu Pro
            370                 375                 380

Tyr Val Arg Cys Lys Leu Pro Asp Asp Phe Ser Glu Asp Leu Asn Leu
385                 390                 395                 400

Asp Tyr Ile Tyr Asp Glu His Gln Asp Gly Ser Ile Phe Pro Gly Leu
                405                 410                 415

His Ser Phe Gln Gly Ala Phe Gln Asn Ala Arg Arg Ile Cys Ala Gly
            420                 425                 430

Val Pro Leu Val Ile His Cys Lys Lys Val Thr Gly Leu Leu Gln Arg
            435                 440                 445

Ala Asp Ala Met Tyr Ala Thr Leu Ala Ala Glu Ala Gly Tyr Thr Val
            450                 455                 460

Asp Ile Ser Lys Ile Asn Glu Val Asp Thr Ala Tyr Ala Ser Ser Val
465                 470                 475                 480

Gly Thr Leu Ala Pro Cys Val Glu Leu Met Ala Ala Lys Lys Tyr
                485                 490                 495

Ala Val Ala Arg Glu Arg Lys Pro Ala Gln Met Ile Leu Gly Ala Val
            500                 505                 510

Gly Gly Pro Asn Ala Asp Ser Ala Ala Phe Tyr Glu Gly Met Ala Leu
            515                 520                 525

Ser Asn Ile Asp Glu Glu Phe Leu Lys Lys Met Cys Ala Val Ala Ser
            530                 535                 540

Ile Lys Tyr Asp Met Leu Met Glu Lys Thr Phe Pro Phe Ala Ala Pro
545                 550                 555                 560

Asp Thr Lys Ile Arg Gln Ala Tyr Ala Phe Ala Lys Ile Ile Asp
            565                 570                 575

Leu Ile Leu Gln Met Leu Thr Gly Pro Leu Gly Tyr Lys Ser Val Pro
            580                 585                 590

Thr Asp Gln Ala Glu Leu Ala Leu Arg Thr Lys Leu Val Arg Gln Leu
            595                 600                 605

His Thr Ala Asp Leu Phe Gly Arg Leu Met Trp Lys Leu Asn Pro Thr
```

```
            610                 615                 620
Lys Leu Asp Arg Val Lys Ala Lys Val Val Lys Leu Ser Asp Pro Thr
625                 630                 635                 640

Lys Arg Trp Ala Asp Asn Lys Ala Leu Tyr Ala Lys Phe Asp Asn Leu
                    645                 650                 655

Gly Asp His Ile Asn Thr Met Leu Leu Ser Val Lys Gly Val Gln Leu
                660                 665                 670

Tyr Phe Asp Thr Gly Thr Val Asn Val Pro Thr Glu Thr Gly Val
                675                 680                 685

Glu Arg Ala Ala Ala Leu Leu Ala Ala Arg Lys Thr Asn Asn His Ala
        690                 695                 700

His Phe Ala Val Cys His Leu Lys Ala Gln Ala Gly Leu Asn Ser Ala
705                 710                 715                 720

Thr Ala Asp Asn Gly Thr Leu Phe Arg Glu Asp Tyr Lys Arg Thr Asp
                    725                 730                 735

Thr Arg Pro Asn Glu Val Val Met Pro Ser Ser Ala Asp Thr Asn Gln
                740                 745                 750

Phe Val Gln Ala Ile Thr Lys Leu Lys Gly Lys Leu Val Phe
                755                 760                 765

<210> SEQ ID NO 13
<211> LENGTH: 699
<212> TYPE: DNA
<213> ORGANISM: koi herpesvirus

<400> SEQUENCE: 13
atgtctcctt tgtgcggtct gttcaagttc gtgctcaggt tcgccttcga cgtcctgatc      60
gccggcgtcg gcgtctacct cgccacgtcg tgcctgtacg acaagggcat gttcaggagg     120
tgccccaaca gcgtgtgcta cgggcacctc agcgtgtggc tcaccgtgtg cgtgatcccc     180
accatcctgg gagccatcgg gtggaccaaa cagttcatgt actgggtcac cctacgcacc     240
agcgcccgtc gcagggccgg cgtgccgcct cgcaagggct gctgcgggtc ctaccgagag     300
gtcctcctcg acgacgtcga cgacgagctg atcgaggccg agcagctcga gcagcagcag     360
cagggcatcg cctcggtggt gaacgggcgc aggcacaaga gcaacagcg gattcctgct      420 ccccagacgc ccatcgtgca gggccagccg tcgacctccg gcacccgcac cacgttggtc     480
ttattcgggc ttgtctgctt tgtgagctac attgcctgga cggccgtctc gcccccgtgc     540
gagtggtaca tctacatcat accggcgctg gtcttctgga agatcctcta ctggctcgtg     600
ggcacctgcg taagctccta caggtactcg cagcgctaca aggacgtgga gagcatcgtc     660
aacgacacgc tgtcccaacg gggttatgag cgcgtatag                            699

<210> SEQ ID NO 14
<211> LENGTH: 232
<212> TYPE: PRT
<213> ORGANISM: koi herpesvirus

<400> SEQUENCE: 14

Met Ser Pro Leu Cys Gly Leu Phe Lys Phe Val Leu Arg Phe Ala Phe
1               5                   10                  15

Asp Val Leu Ile Ala Gly Val Gly Val Tyr Leu Ala Thr Ser Cys Leu
                20                  25                  30

Tyr Asp Lys Gly Met Phe Arg Arg Cys Pro Asn Ser Val Cys Tyr Gly
            35                  40                  45

His Leu Ser Val Trp Leu Thr Val Cys Val Ile Pro Thr Ile Leu Gly
        50                  55                  60
```

```
Ala Ile Gly Trp Thr Lys Gln Phe Met Tyr Trp Val Thr Leu Arg Thr
 65                  70                  75                  80

Ser Ala Arg Arg Arg Ala Gly Val Pro Pro Arg Lys Gly Cys Cys Gly
                 85                  90                  95

Ser Tyr Arg Glu Val Leu Leu Asp Asp Val Asp Glu Leu Ile Glu
            100                 105                 110

Ala Glu Gln Leu Glu Gln Gln Gln Gly Ile Ala Ser Val Val Asn
        115                 120                 125

Gly Arg Arg His Lys Lys Gln Gln Arg Ile Pro Ala Pro Gln Thr Pro
130                 135                 140

Ile Val Gln Gly Gln Pro Ser Thr Ser Gly Thr Arg Thr Thr Leu Val
145                 150                 155                 160

Leu Phe Gly Leu Val Cys Phe Val Ser Tyr Ile Ala Trp Thr Ala Val
                165                 170                 175

Ser Pro Pro Cys Glu Trp Tyr Ile Tyr Ile Pro Ala Leu Val Phe
            180                 185                 190

Trp Lys Ile Leu Tyr Trp Leu Val Gly Thr Cys Val Ser Ser Tyr Arg
        195                 200                 205

Tyr Ser Gln Arg Tyr Lys Asp Val Glu Ser Ile Val Asn Asp Thr Leu
210                 215                 220

Ser Gln Arg Gly Tyr Glu Arg Val
225                 230
```

<210> SEQ ID NO 15
<211> LENGTH: 966
<212> TYPE: DNA
<213> ORGANISM: koi herpesvirus

<400> SEQUENCE: 15

```
atgagcgcgt ataggtacaa caggttgagg gacgagggcg agggcgaaga gggcgagggc      60
gagggcgagg ggccccgaga cggcggcgac gagagacggg atggggcgg cggcggaggc     120
ggcggcgagg gcaagggccc ccgctactac tacaacagcc ggggcaggct caagcgcgcg     180
gaccggcccg ggctggacgt gatcctcacg ggcctcttca ccttcggctg gtcctcgtg     240
accatcagcg tgtttgtgct cgatcgctct cacccccacc cgacggcgg cggcggcggc     300
gacaacccgc acgccgtggc ctcggtggtg caggggtca tcggcctgct cggggagaac     360
ggctcctccg acaacatcag cggcatcagc atcggcggca acggaggcgc tgcggcggac     420
cctccgctcc actgtttcga cggcggcatc tcggccatga gggcgacgat gctatcggtg     480
tgcctggcca acctggccac ctacctcttc aagctcaccg tgttttttca gtttgtggtc     540
gcctccgtca aggagtacgc ggcgctgcac tcggacgggg ccatcatgtc gaccgctgcg     600
ggcctccgcg aggacacgct cgagcacatg cagagggccc gctgggtcgc gctcgccctg     660
gtccggatag cccttttccc gatggccctg gctcatctgg ccgcagcggc caccctgcag     720
cgcatgaacc ctcacatgcg agcctacgcg agcgccaccg agagcgaccc gtcccagcgc     780
agcttctgct tcagagtgta cctcttctac accctcgtgt gcgggcaggc ctgcgtgagc     840
ctctttgccg ggatcctggc cgtcatcaag acggtcagcg gcgtggacga caagagcacc     900
cggagacaga tcaggaaccg tctcgagaac caaaacatta cccgcatcct caacgagctc     960
gtctga                                                                966
```

<210> SEQ ID NO 16
<211> LENGTH: 320
<212> TYPE: PRT

<213> ORGANISM: koi herpesvirus

<400> SEQUENCE: 16

```
Ser Ala Tyr Arg Tyr Asn Arg Leu Arg Asp Glu Gly Glu Gly Glu
1               5                   10                  15
Glu Gly Glu Gly Glu Gly Pro Arg Asp Gly Gly Asp Glu Arg Arg
                20                  25                  30
Asp Gly Gly Gly Gly Gly Gly Glu Gly Lys Gly Pro Arg Tyr
            35                  40                  45
Tyr Tyr Asn Ser Arg Gly Arg Leu Lys Arg Ala Asp Arg Pro Gly Leu
        50                  55                  60
Asp Val Ile Leu Thr Gly Leu Phe Thr Phe Gly Trp Val Leu Val Thr
65                  70                  75                  80
Ile Ser Val Phe Val Leu Asp Arg Ser His Pro His His Asp Gly Gly
                85                  90                  95
Gly Gly Gly Asp Asn Pro His Ala Val Ala Ser Val Val Gln Gly Val
            100                 105                 110
Ile Gly Leu Leu Gly Glu Asn Gly Ser Ser Asp Asn Ile Ser Gly Ile
        115                 120                 125
Ser Ile Gly Gly Asn Gly Gly Ala Ala Ala Asp Pro Pro Leu His Cys
130                 135                 140
Phe Asp Gly Gly Ile Ser Ala Met Arg Ala Thr Met Leu Ser Val Cys
145                 150                 155                 160
Leu Ala Asn Leu Ala Thr Tyr Leu Phe Lys Leu Thr Val Phe Phe Gln
                165                 170                 175
Phe Val Val Ala Ser Val Lys Glu Tyr Ala Ala Leu His Ser Asp Gly
            180                 185                 190
Ala Ile Met Ser Thr Ala Ala Gly Leu Arg Glu Asp Thr Leu Glu His
        195                 200                 205
Met Gln Arg Ala Arg Trp Val Ala Leu Ala Leu Val Arg Ile Ala Leu
210                 215                 220
Phe Pro Met Ala Leu Ala His Leu Ala Ala Ala Thr Leu Gln Arg
225                 230                 235                 240
Met Asn Pro His Met Arg Ala Tyr Ala Ser Ala Thr Glu Ser Asp Pro
                245                 250                 255
Ser Gln Arg Ser Phe Cys Phe Arg Val Tyr Leu Phe Tyr Thr Leu Val
            260                 265                 270
Cys Gly Gln Ala Cys Val Ser Leu Phe Ala Gly Ile Leu Ala Val Ile
        275                 280                 285
Lys Thr Val Ser Gly Val Asp Asp Lys Ser Thr Arg Arg Gln Ile Arg
290                 295                 300
Asn Arg Leu Glu Asn Gln Asn Ile Thr Arg Ile Leu Asn Glu Leu Val
305                 310                 315                 320
```

<210> SEQ ID NO 17
<211> LENGTH: 771
<212> TYPE: DNA
<213> ORGANISM: koi herpesvirus

<400> SEQUENCE: 17

```
atggcagtca ccaaagctca actggccaag agagccaaaa aaatcggcac cgccctgatg    60
aacaaggtgc ccactgcgtc ggcgagcaag ctcctcgtca agcttccgt agacgctgag    120
cgattcaaga tactcgtcgc aactgtcacg caggtcatct gtccaatgtt tgccccgctg   180
acgatgggca ttgcgcacgc catgtactcc aacgatccca actttgatct caacggcgcc   240
```

```
ttcatcggca tcggaatctt cggtgccctc gtcttcctcg tcctcctcgg aaccttcatc    300
atgctctgct accggtgcgt gaagggaggc cacagcatgt tcatgctgat gaggcccgtg    360
ttggcgctgt ttatcctcaa catcttcctc ttcctgatcg gggtcatcta cgccggcatc    420
aacctgctgt gcaagacggt cacctactcg aagacggcgg tgtgcgtgtc tcagaacgcc    480
atgtccctgg ccgtgctgga gctcttcacc gcctgcctga tcctcctcaa agagacccct    540
tacagcggcc tgcgcatggc cgagatcaag gcccgcgtga gcggcggcgc tatggagtac    600
gaaggaagcg acgacgaata ctactacaac tcctaccaga acgtagcgga gggcctccag    660
aggtctatgc gcgactatca ggacgacgag gattttctg acccagacac tgagagcgtc    720
atcggtcagg cctccaaaat cccacgcaag tacaccggca agatgtggtg a            771
```

<210> SEQ ID NO 18
<211> LENGTH: 646
<212> TYPE: PRT
<213> ORGANISM: koi herpesvirus

<400> SEQUENCE: 18

```
Leu Lys Arg Leu Leu Cys Phe Val Val Leu Ala Ser Thr Val Gly Trp
 1               5                  10                  15

Trp Trp Trp Arg Arg Leu Arg Glu Ala Ser Glu Ser Pro His Leu Ala
                20                  25                  30

Gly Val Leu Ala Trp Asp Phe Gly Gly Leu Thr Asp Asp Ala Leu Ser
            35                  40                  45

Val Trp Val Arg Lys Ile Leu Val Val Leu Ile Val Ala His Arg Pro
        50                  55                  60

Leu Glu Ala Leu Arg Tyr Val Leu Val Gly Val Val Val Phe Val
 65                  70                  75                  80

Val Ala Ser Phe Val Leu His Ser Ala Ala Ala His Ala Gly Leu Asp
                85                  90                  95

Leu Gly His Ala Gln Ala Ala Val Lys Gly Leu Phe Glu Glu Asp Gln
                100                 105                 110

Ala Gly Gly Glu Glu Leu Gln His Gly Gln Gly His Gly Val Leu Arg
            115                 120                 125

His Ala His Arg Arg Leu Arg Val Gly Asp Arg Leu Ala Gln Gln Val
        130                 135                 140

Asp Ala Gly Val Asp Asp Pro Asp Gln Glu Glu Asp Val Glu Asp
145                 150                 155                 160

Lys Gln Arg Gln His Gly Pro His Gln His Glu His Ala Val Ala Ser
                165                 170                 175

Leu His Ala Pro Val Ala Glu His Asp Glu Gly Ser Glu Glu Asp Glu
            180                 185                 190

Glu Asp Glu Gly Thr Glu Asp Ser Asp Ala Asp Glu Gly Ala Val Glu
        195                 200                 205

Ile Lys Val Gly Ile Val Gly Val His Gly Val Arg Asn Ala His Arg
    210                 215                 220

Gln Arg Gly Lys His Trp Thr Asp Asp Leu Arg Asp Ser Cys Asp Glu
225                 230                 235                 240

Tyr Leu Glu Ser Leu Ser Val Tyr Gly Lys Leu Asp Glu Leu Ala
                245                 250                 255

Arg Arg Arg Ser Gly His Leu Val His Gln Gly Gly Ala Asp Phe Phe
            260                 265                 270

Gly Ser Leu Gly Gln Leu Ser Phe Gly Asp Cys His Glu Asp Glu Asp
        275                 280                 285
```

```
Ser His Asn Leu Thr Ser Val Glu Met Asp Ala Pro Val Phe Ser Ser
            290                 295                 300
Ala Ala Leu Lys Cys Gly Asn Gly Glu Leu Pro Arg Ala Val Val Glu
305                 310                 315                 320
Pro Gly Ser Arg Asp Val Gly Ile Thr Lys Asn Leu Ser Tyr Leu Tyr
                325                 330                 335
Pro Thr Ser Ser Leu Tyr Arg Ala Lys Gln Arg Ile Pro Ile Lys Leu
            340                 345                 350
Glu Ile Asp Gly Leu Gln Gln Asp Val Ser Glu Arg Leu Ala Lys Ile
        355                 360                 365
Leu Gln Gly Arg Ile Trp Thr Lys Pro Gln Leu Ser Thr Glu Leu Leu
370                 375                 380
Lys Gln Leu Pro Glu Ala Cys Arg Asp Arg Ala Glu Asp Leu Ala Asp
385                 390                 395                 400
Ser Ala Ala Glu Val Leu Ser His Ala Ala Pro Phe Thr Val His Ser
                405                 410                 415
Val Arg Gln Ala Leu Ile Arg Ser Leu Phe Tyr Val Arg Val Gly Thr
            420                 425                 430
Leu Val Asp Thr Leu Val Lys Arg Glu Phe His Ser Arg Arg Gly Pro
        435                 440                 445
Ile Val Ala Ser Leu Tyr Arg Ser Tyr Gly Trp Arg Pro Ile Asp Ala
450                 455                 460
Gly Ile Ala Val Thr Ser Arg Arg Pro Gln Gly His Arg Cys Arg Val
465                 470                 475                 480
Cys Gly Asp Val Ser Pro Ala Ala Phe Asp Gly Asn His His Gly Thr
                485                 490                 495
Glu Leu Asp Gly Val Ala Thr Asp Ala Glu Gly Asn Phe Ile Leu Val
            500                 505                 510
Glu Ile Lys Thr His Gly Gly Ala Thr Val Ser Ala Ala Leu Leu Asn
        515                 520                 525
Arg Tyr Lys Thr Gln Thr Trp Ile Gly Glu Cys Met Phe Arg His Thr
530                 535                 540
Phe Gly Leu Cys Cys Ser Ser Asn Val His Ser Tyr Ile Val Phe Val
545                 550                 555                 560
Ser Pro Ser Thr Tyr Thr Ile Asp Ser Val Ile Gln Val Pro Ala Val
                565                 570                 575
Pro Lys Arg Leu His Pro Arg Leu Phe Ser Val Phe Pro Ser Leu Pro
            580                 585                 590
Asn Leu Cys Phe Val Arg Arg Thr Gln Lys Pro Lys Arg Pro Ala Ala
        595                 600                 605
Ala Gln Arg Pro Ala Lys Thr Pro Gly Asp Arg Pro Ala Arg Pro Ser
610                 615                 620
Ser Ser Ala Gly Gln Thr Ala Ala Lys Gln Tyr Pro His Arg Tyr Tyr
625                 630                 635                 640
Lys Arg Lys Thr Ala Ala
                645

<210> SEQ ID NO 19
<211> LENGTH: 1053
<212> TYPE: DNA
<213> ORGANISM: koi herpesvirus

<400> SEQUENCE: 19
atggatgcac cggtcttctc ctccgctgct ctcaagtgcg gcaacggcga gctacctagg    60
gcggtggtgg aacctggctc ccgcgatgtg ggtatcacca agaatctttc gtacctttac   120
```

```
ccgacgtcta gcttgtacag ggccaagcag cggattccga ttaaacttga gatcgacggt      180
ctccaacaag atgtgtccga gcgcctggct aaaattttac aaggtcggat ttggactaaa      240
ccacaattaa gtacggagct cctcaagcag ctaccggagg cgtgcaggga tagggccgag      300
gacctggccg atagcgccgc cgaggtcctg tcccacgcgg cgcccttcac cgtccactcg      360
gtccgccagg ccctcatcag gtccctcttc tacgtgagag tggggacgct ggtggacacg      420
ctcgtcaagc gcgagttcca tagcaggagg ggacccatcg tcgccagcct ctaccgctcc      480
tacggctgga gacccatcga cgccggcatc gccgtcacct ccaggagacc tcagggacac      540
cgctgcagag tttgtggaga cgtctccccg gcagccttcg acggtaacca ccacggcaca      600
gagctggacg gcgtcgccac cgacgcggag ggcaacttta tcctcgtcga gatcaagacc      660
cacggaggcg ccaccgtcag cgccgctctc ctcaaccgct acaagaccca gacctggata      720
ggcgagtgca tgttcaggca cacgttcggc ctctgctgct ccagcaacgt ccacagctac      780
atcgtctttg tcagccccag cacctacacc atcgacagct gatccaggt ccccgctgtg      840
cccaagcgcc tccaccccag actcttctcc gtgttcccctt ccctccccaa cctctgcttc      900
gtcaggcgga ctcagaaacc caagaggcct gctgctgcgc agagacctgc gaaaactcct      960
ggagacagac ccgctcgacc ttcctcctca gcaggacaga cggcggcgaa gcagtacccg     1020
caccgctact acaagaggaa gacagccgcc tga                                  1053
```

<210> SEQ ID NO 20
<211> LENGTH: 350
<212> TYPE: PRT
<213> ORGANISM: koi herpesvirus

<400> SEQUENCE: 20

```
Met Asp Ala Pro Val Phe Ser Ser Ala Ala Leu Lys Cys Gly Asn Gly
1               5                   10                  15

Glu Leu Pro Arg Ala Val Val Glu Pro Gly Ser Arg Asp Val Gly Ile
            20                  25                  30

Thr Lys Asn Leu Ser Tyr Leu Tyr Pro Thr Ser Ser Leu Tyr Arg Ala
        35                  40                  45

Lys Gln Arg Ile Pro Ile Lys Leu Glu Ile Asp Gly Leu Gln Gln Asp
    50                  55                  60

Val Ser Glu Arg Leu Ala Lys Ile Leu Gln Gly Arg Ile Trp Thr Lys
65                  70                  75                  80

Pro Gln Leu Ser Thr Glu Leu Leu Lys Gln Leu Pro Glu Ala Cys Arg
                85                  90                  95

Asp Arg Ala Glu Asp Leu Ala Asp Ser Ala Ala Glu Val Leu Ser His
            100                 105                 110

Ala Ala Pro Phe Thr Val His Ser Val Arg Gln Ala Leu Ile Arg Ser
        115                 120                 125

Leu Phe Tyr Val Arg Val Gly Thr Leu Val Asp Thr Leu Val Lys Arg
    130                 135                 140

Glu Phe His Ser Arg Arg Gly Pro Ile Val Ala Ser Leu Tyr Arg Ser
145                 150                 155                 160

Tyr Gly Trp Arg Pro Ile Asp Ala Gly Ile Ala Val Thr Ser Arg Arg
                165                 170                 175

Pro Gln Gly His Arg Cys Arg Val Cys Gly Asp Val Ser Pro Ala Ala
            180                 185                 190

Phe Asp Gly Asn His His Gly Thr Glu Leu Asp Gly Val Ala Thr Asp
        195                 200                 205
```

-continued

```
Ala Glu Gly Asn Phe Ile Leu Val Glu Ile Lys Thr His Gly Gly Ala
    210                 215                 220

Thr Val Ser Ala Ala Leu Leu Asn Arg Tyr Lys Thr Gln Thr Trp Ile
225                 230                 235                 240

Gly Glu Cys Met Phe Arg His Thr Phe Gly Leu Cys Cys Ser Ser Asn
                245                 250                 255

Val His Ser Tyr Ile Val Phe Val Ser Pro Ser Thr Tyr Thr Ile Asp
            260                 265                 270

Ser Val Ile Gln Val Pro Ala Val Pro Lys Arg Leu His Pro Arg Leu
        275                 280                 285

Phe Ser Val Phe Pro Ser Leu Pro Asn Leu Cys Phe Val Arg Arg Thr
    290                 295                 300

Gln Lys Pro Lys Arg Pro Ala Ala Ala Gln Arg Pro Ala Lys Thr Pro
305                 310                 315                 320

Gly Asp Arg Pro Ala Arg Pro Ser Ser Ser Ala Gly Gln Thr Ala Ala
                325                 330                 335

Lys Gln Tyr Pro His Arg Tyr Tyr Lys Arg Lys Thr Ala Ala
            340                 345                 350
```

<210> SEQ ID NO 21
<211> LENGTH: 20
<212> TYPE: DNA
<213> ORGANISM: Artificial Sequence
<220> FEATURE:
<223> OTHER INFORMATION: KHV-g1-F

<400> SEQUENCE: 21
atgcctgcca cctttggcag          20

<210> SEQ ID NO 22
<211> LENGTH: 20
<212> TYPE: DNA
<213> ORGANISM: Artificial Sequence
<220> FEATURE:
<223> OTHER INFORMATION: KHV-g1-R

<400> SEQUENCE: 22
tcaccccgca gaggtaccat          20

<210> SEQ ID NO 23
<211> LENGTH: 20
<212> TYPE: DNA
<213> ORGANISM: Artificial Sequence
<220> FEATURE:
<223> OTHER INFORMATION: KHV-g2-F

<400> SEQUENCE: 23
atgtaccagc agcaatacca          20

<210> SEQ ID NO 24
<211> LENGTH: 20
<212> TYPE: DNA
<213> ORGANISM: Artificial Sequence
<220> FEATURE:
<223> OTHER INFORMATION: KHV-g2-R

<400> SEQUENCE: 24
tcagttgtga agagtagatt          20

<210> SEQ ID NO 25
<211> LENGTH: 20
<212> TYPE: DNA
<213> ORGANISM: Artificial Sequence

```
<220> FEATURE:
<223> OTHER INFORMATION: KHV-g3-F

<400> SEQUENCE: 25
atgagccaca gacagccagc                                              20

<210> SEQ ID NO 26
<211> LENGTH: 20
<212> TYPE: DNA
<213> ORGANISM: Artificial Sequence
<220> FEATURE:
<223> OTHER INFORMATION: KHV-g3-R

<400> SEQUENCE: 26
tcagtaatag taatagttgt                                              20

<210> SEQ ID NO 27
<211> LENGTH: 20
<212> TYPE: DNA
<213> ORGANISM: Artificial Sequence
<220> FEATURE:
<223> OTHER INFORMATION: KHV-g4-F

<400> SEQUENCE: 27
atgccgtcga gcatgactgg                                              20

<210> SEQ ID NO 28
<211> LENGTH: 20
<212> TYPE: DNA
<213> ORGANISM: Artificial Sequence
<220> FEATURE:
<223> OTHER INFORMATION: KHV-g4-R

<400> SEQUENCE: 28
tcagagttcg tctctgatgg                                              20

<210> SEQ ID NO 29
<211> LENGTH: 20
<212> TYPE: DNA
<213> ORGANISM: Artificial Sequence
<220> FEATURE:
<223> OTHER INFORMATION: KHV-g5-F

<400> SEQUENCE: 29
atgtctatgc gcccgcacaa                                              20

<210> SEQ ID NO 30
<211> LENGTH: 20
<212> TYPE: DNA
<213> ORGANISM: Artificial Sequence
<220> FEATURE:
<223> OTHER INFORMATION: KHV-g5-R

<400> SEQUENCE: 30
ctaccgagtg agccgtctct                                              20

<210> SEQ ID NO 31
<211> LENGTH: 20
<212> TYPE: DNA
<213> ORGANISM: Artificial Sequence
<220> FEATURE:
<223> OTHER INFORMATION: KHV-m1-F

<400> SEQUENCE: 31
atgacggagc gggcagcgct                                              20
```

```
<210> SEQ ID NO 32
<211> LENGTH: 20
<212> TYPE: DNA
<213> ORGANISM: Artificial Sequence
<220> FEATURE:
<223> OTHER INFORMATION: KHV-m1-R

<400> SEQUENCE: 32
ttagaagacg agcaagccct                                          20

<210> SEQ ID NO 33
<211> LENGTH: 20
<212> TYPE: DNA
<213> ORGANISM: Artificial Sequence
<220> FEATURE:
<223> OTHER INFORMATION: KHV-m2-F

<400> SEQUENCE: 33
atgtctcctt tgtgcggtct                                          20

<210> SEQ ID NO 34
<211> LENGTH: 20
<212> TYPE: DNA
<213> ORGANISM: Artificial Sequence
<220> FEATURE:
<223> OTHER INFORMATION: KHV-m2-R

<400> SEQUENCE: 34
ctatacgcgc tcataacccc                                          20

<210> SEQ ID NO 35
<211> LENGTH: 20
<212> TYPE: DNA
<213> ORGANISM: Artificial Sequence
<220> FEATURE:
<223> OTHER INFORMATION: KHV-m3-F

<400> SEQUENCE: 35
atgagcgcgt ataggtacaa                                          20

<210> SEQ ID NO 36
<211> LENGTH: 20
<212> TYPE: DNA
<213> ORGANISM: Artificial Sequence
<220> FEATURE:
<223> OTHER INFORMATION: KHV-m3-R

<400> SEQUENCE: 36
tcagacgagc tcgttgagga                                          20

<210> SEQ ID NO 37
<211> LENGTH: 20
<212> TYPE: DNA
<213> ORGANISM: Artificial Sequence
<220> FEATURE:
<223> OTHER INFORMATION: KHV-m4-F

<400> SEQUENCE: 37
atggcagtca ccaaagctca                                          20

<210> SEQ ID NO 38
<211> LENGTH: 20
<212> TYPE: DNA
<213> ORGANISM: Artificial Sequence
<220> FEATURE:
<223> OTHER INFORMATION: KHV-m4-R

<400> SEQUENCE: 38
```

-continued

```
tcaccacatc ttgccggtgt                                                 20

<210> SEQ ID NO 39
<211> LENGTH: 20
<212> TYPE: DNA
<213> ORGANISM: Artificial Sequence
<220> FEATURE:
<223> OTHER INFORMATION: KHV-m5-F

<400> SEQUENCE: 39
atggatgcac cggtcttctc                                                 20

<210> SEQ ID NO 40
<211> LENGTH: 20
<212> TYPE: DNA
<213> ORGANISM: Artificial Sequence
<220> FEATURE:
<223> OTHER INFORMATION: KHV-m5-R

<400> SEQUENCE: 40
tcaggcggct gtcttcctct                                                 20
```